(12) United States Patent
Stewart et al.

(10) Patent No.: US 12,127,778 B2
(45) Date of Patent: Oct. 29, 2024

(54) FOCAL PULSED FIELD ABLATION DEVICES AND METHODS

(71) Applicant: Medtronic, Inc., Minneapolis, MN (US)

(72) Inventors: Mark T. Stewart, Lino Lakes, MN (US); Brian T. Howard, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 596 days.

(21) Appl. No.: 16/263,812

(22) Filed: Jan. 31, 2019

(65) Prior Publication Data

US 2019/0254735 A1  Aug. 22, 2019

Related U.S. Application Data

(60) Provisional application No. 62/633,393, filed on Feb. 21, 2018.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC .......... *A61B 18/1206* (2013.01); *A61B 18/14* (2013.01); *A61B 18/1492* (2013.01);
(Continued)

(58) Field of Classification Search
CPC . A61B 18/1206; A61B 18/14; A61B 18/1492; A61B 2218/007;
(Continued)

(56) References Cited

U.S. PATENT DOCUMENTS

| | | |
|---|---|---|
| 6,264,650 B1 | 7/2001 | Hovda et al. |
| 6,464,695 B2 | 10/2002 | Hovda et al. |

(Continued)

FOREIGN PATENT DOCUMENTS

| | | | |
|---|---|---|---|
| EP | 1003432 | 5/2000 | |
| EP | 1003432 A1 * | 5/2000 | ......... A61B 18/1482 |

(Continued)

OTHER PUBLICATIONS

International Search Report and Written Opinion dated Apr. 23, 2019, for corresponding International Application No. PCT/US2019/016048; International Filing Date: Jan. 31, 2019 consisting of 12-pages.

(Continued)

*Primary Examiner* — Khadijeh A Vahdat
(74) *Attorney, Agent, or Firm* — Michael Best & Friedrich LLP

(57) ABSTRACT

Devices, systems, and methods for more efficiently ablating tissue with pulsed field ablation energy while minimizing collateral injury to non-target tissue. In one embodiment, a system for ablating tissue at a treatment site comprises: an energy delivery device; and a control unit including: a source of impedance-modifying fluid in fluid communication with the energy delivery device; an energy generator in electrical communication with the energy delivery device, the energy generator being configured to transmit energy to the energy delivery device and the energy delivery device being configured to deliver energy to the treatment site; and processing circuitry configured to control delivery of the impedance-modifying fluid from the energy delivery device to the treatment site. In one embodiment, a method for ablating tissue comprises delivering an impedance-modifying fluid to a treatment site and delivering pulsed field ablation energy to the treatment site.

18 Claims, 11 Drawing Sheets

(52) U.S. Cl.
CPC ............... *A61B 2018/00214* (2013.01); *A61B 2018/00351* (2013.01); *A61B 2018/00363* (2013.01); *A61B 2018/00577* (2013.01); *A61B 2018/00613* (2013.01); *A61B 2018/00744* (2013.01); *A61B 2018/00791* (2013.01); *A61B 2018/00839* (2013.01); *A61B 2018/00875* (2013.01); *A61B 2018/00892* (2013.01); *A61B 2018/126* (2013.01); *A61B 2018/1472* (2013.01); *A61B 2218/002* (2013.01); *A61B 2218/007* (2013.01)

(58) Field of Classification Search
CPC .... A61B 2018/00791; A61B 2218/002; A61B 2018/00363; A61B 2018/00613; A61B 2018/00892; A61B 2018/1472; A61B 2018/00744; A61B 2018/00839; A61B 2018/00214; A61B 2018/00351; A61B 2018/00577; A61B 2018/00875; A61B 2018/126
USPC .......................................................... 606/41
See application file for complete search history.

(56) References Cited

U.S. PATENT DOCUMENTS

| | | | |
|---|---|---|---|
| 6,468,270 | B1 | 10/2002 | Hovda et al. |
| 6,632,193 | B1 | 10/2003 | Davison et al. |
| 6,855,143 | B2 | 2/2005 | Davison et al. |
| 7,276,063 | B2 | 10/2007 | Davison et al. |
| 7,311,708 | B2 | 12/2007 | McClurken |
| 7,331,956 | B2 | 2/2008 | Hovda et al. |
| 7,435,247 | B2 | 10/2008 | Woloszko et al. |
| 7,537,595 | B2 | 5/2009 | McClurken |
| 7,572,251 | B1 | 8/2009 | Davison et al. |
| 7,678,069 | B1 | 3/2010 | Baker et al. |
| 7,708,733 | B2 | 5/2010 | Sanders et al. |
| 7,758,537 | B1 | 7/2010 | Brunell et al. |
| 8,414,579 | B2 * | 4/2013 | Kim .................. A61B 18/1492 606/41 |
| 8,801,705 | B2 | 8/2014 | Sanders et al. |
| 2001/0001314 | A1 | 5/2001 | Davison et al. |
| 2001/0029370 | A1 | 10/2001 | Hodva et al. |
| 2002/0111618 | A1* | 8/2002 | Stewart ............. A61B 18/1492 606/41 |
| 2002/0151884 | A1* | 10/2002 | Hoey .................... A61B 18/18 606/41 |
| 2003/0216733 | A1* | 11/2003 | McClurken ........... A61B 18/14 606/51 |
| 2005/0033278 | A1 | 2/2005 | McClurken et al. |
| 2005/0070894 | A1* | 3/2005 | McClurken ........ A61B 18/1492 606/50 |
| 2005/0090816 | A1* | 4/2005 | McClurken ............ A61B 17/32 606/49 |
| 2005/0090818 | A1* | 4/2005 | Pike, Jr. ............. A61B 18/1492 606/41 |
| 2005/0288730 | A1* | 12/2005 | Deem ................ A61N 1/36057 607/42 |
| 2006/0009756 | A1* | 1/2006 | Francischelli ..... A61B 18/1815 606/41 |
| 2007/0208337 | A1* | 9/2007 | Podhajsky ........... A61B 18/042 606/49 |
| 2008/0097429 | A1 | 4/2008 | McClurken |
| 2010/0211064 | A1* | 8/2010 | Mahapatra ......... A61B 18/1492 606/41 |
| 2010/0222859 | A1* | 9/2010 | Govari ............... A61B 18/1492 607/119 |
| 2012/0265276 | A1* | 10/2012 | Curley .................... F04B 41/02 607/105 |
| 2013/0030426 | A1* | 1/2013 | Gallardo ............ A61B 18/1492 606/41 |
| 2014/0163550 | A1 | 6/2014 | Besser et al. |
| 2015/0238729 | A1* | 8/2015 | Jenson .................. A61M 25/04 604/510 |
| 2017/0035499 | A1* | 2/2017 | Stewart .................... A61N 1/327 |
| 2017/0224415 | A1* | 8/2017 | Dong ................ A61B 18/1492 |
| 2019/0008585 | A1* | 1/2019 | Dong ................ A61B 18/1492 |
| 2019/0069949 | A1* | 3/2019 | Vrba ..................... A61B 18/02 |
| 2019/0274757 | A1* | 9/2019 | Mahapatra ........ A61M 25/0147 |

FOREIGN PATENT DOCUMENTS

| | | |
|---|---|---|
| EP | 2204133 A1 | 7/2010 |
| EP | 2275050 A1 | 1/2011 |
| WO | 2017067517 A1 | 4/2017 |

OTHER PUBLICATIONS

European Patent Office Examination Report for Application No. 19705669.0 dated May 6, 2024 (4 pages).

* cited by examiner

FOCAL PULSED FIELD ABLATION DEVICES AND METHODS

CROSS-REFERENCE TO RELATED APPLICATION

This application is related to and claims the benefit of U.S. Application Ser. No. 62/633,393, filed Feb. 21, 2018.

FIELD

The present technology is generally related to devices, systems, and methods for more efficiently ablating tissue with pulsed field ablation energy while minimizing collateral injury to non-targeted tissue. In one embodiment, a system for ablating tissue at a treatment site comprises: an energy delivery device; and a control unit including: a source of impedance-modifying fluid in fluid communication with the energy delivery device; an energy generator in electrical communication with the energy delivery device, the energy generator being configured to transmit energy to the energy delivery device and the energy delivery device being configured to deliver energy to the treatment site; and processing circuitry configured to control delivery of the impedance-modifying fluid from the energy delivery device to the treatment site.

BACKGROUND

Tissue ablation is a medical procedure commonly used to treat conditions such as cardiac arrhythmia, which includes atrial fibrillation. For treating cardiac arrhythmia, ablation can be performed to modify tissue, such as to stop aberrant electrical propagation and/or disrupt aberrant electrical conduction through cardiac tissue. Although thermal ablation techniques are frequency used, such as cryoablation and radiofrequency (RF) ablation, non-thermal techniques such as pulsed field ablation (PFA) may also be used.

Pulsed field ablation involves the application of short pulsed electric fields (PEF), which may reversibly or irreversibly destabilize cell membranes through electropermeabilization, but generally do not affect the structural integrity of the tissue components, including the acellular cardiac extracellular matrix. The nature of PFA allows for very brief periods of therapeutic energy delivery, on the order of tens of milliseconds in duration. Further, PFA may not cause collateral damage to non-targeted tissue as frequently or severely as thermal ablation techniques. Additionally, pharmacologic agents may be preferentially introduced into the cells of targeted tissue that are exposed to PEF having reversible membrane permeabilization.

Pulsed electric field ablation therapy may be safely delivered from virtually any intracardiac device electrode or set of electrodes, assuming the electrode(s) have sufficient surface area and inter-electrode spacing to avoid localized heating when delivering in a bipolar manner between electrodes. Devices such as irrigated catheters may be used to deliver pulsed electric field energy, but they generally have a relatively small surface area. High energy levels may also increase the risk of thromboembolic events. Further, at least some of the delivered pulsed field ablation energy unintentionally may be directed toward non-target tissue. For example, even when the electrode(s) are in contact with the target tissue, at least some of the delivered energy will pass into the blood pool instead of the target tissue. When high voltages are applied to electrodes in a blood-tissue environment, such as when trying to create a deep lesion in cardiac muscle, a relatively high current may be driven into both the blood and the targeted tissue. If such a current is above the threshold at which substantial heat is generated at the blood-electrode interface, an undesirable release of gas bubbles and hemolysis may occur. These bubbles and/or thermally denatured blood proteins may be released as emboli that are injurious to the patient.

SUMMARY

The techniques of this disclosure generally relate to devices, systems, and methods for more efficiently ablating tissue with pulsed field ablation energy while minimizing total energy delivered and collateral injury to non-targeted tissue. In one embodiment, a system for ablating tissue at a treatment site comprises: an energy delivery device; and a control unit including: a source of impedance-modifying fluid in fluid communication with the energy delivery device; an energy generator in electrical communication with the energy delivery device, the energy generator being configured to transmit energy to the energy delivery device and the energy delivery device being configured to deliver energy to the treatment site; and processing circuitry configured to control delivery of the impedance-modifying fluid from the energy delivery device to the treatment site.

In one aspect of the embodiment, the processing circuitry is configured to control delivery of the impedance-modifying fluid from the energy delivery device such that the energy delivery device delivers the impedance-modifying fluid to the treatment site before an onset of the delivery of energy from the energy delivery device to the treatment site. In one aspect of the embodiment, the energy delivery device delivers the impedance-modifying fluid to the treatment site at a flow rate of between approximately 1 mL/min to approximately 120 mL/min (approximately 2 mL/sec). In one aspect of the embodiment, the energy delivery device delivers the impedance-modifying fluid to the treatment site approximately two seconds before the onset of the delivery of energy from the energy delivery device to the treatment site.

In one aspect of the embodiment, the processing circuitry is configured to control delivery of the impedance-modifying fluid from the energy delivery device such that the energy delivery device delivers the impedance-modifying fluid to the treatment site simultaneously with an onset of the delivery of energy from the energy delivery device to the treatment site.

In one aspect of the embodiment, the impedance-modifying fluid is a hypotonic fluid. In one aspect of the embodiment, the hypotonic fluid is an aqueous solution of saline including less than 0.9% by weight of sodium chloride.

In one embodiment, the hypotonic fluid includes at least one of glucose, dextrose, calcium, calcium gluconate, and calcium chloride.

In one aspect of the embodiment, the impedance-modifying fluid is a hypertonic fluid.

In one aspect of the embodiment, the energy delivery device includes at least one irrigation port in fluid communication with the source of impedance-modifying fluid. In one aspect of the embodiment, the energy delivery device further includes at least one energy delivery electrode, the at least one irrigation port being at least one of in the at least one energy delivery electrode and in close proximity to the at least one energy delivery electrode.

In one aspect of the embodiment, each of the at least one energy delivery electrode has a first edge and a second edge opposite the first edge, the at least one irrigation port being in the energy delivery electrode immediately proximate at least one of the first edge and the second edge.

In one aspect of the embodiment, the energy delivery device further includes an electrode-bearing structure to which the at least one energy delivery electrode is coupled, the at least one irrigation port being in the electrode-bearing structure.

In one aspect of the embodiment, the source of impedance-modifying fluid is a source of a first impedance-modifying fluid, the control unit further including a source of a second impedance-modifying fluid in fluid communication with the energy delivery device. In one aspect of the embodiment, the first impedance-modifying fluid is a hypotonic fluid and the second impedance-modifying fluid is a hypertonic fluid, the processing circuitry being configured to control delivery of the first and second impedance-modifying fluids from the energy delivery device such that the energy delivery device delivers the first impedance-modifying fluid to a first portion of the treatment site and delivers the second impedance-modifying fluid to a second portion of the treatment site simultaneously.

In one aspect of the embodiment, the first impedance-modifying fluid is a hypotonic fluid and the second impedance-modifying fluid is a hypertonic fluid, the energy delivery device being configured to deliver first and second impedance-modifying fluids together as a mixture, the processing circuitry being configured to modify the amount of at least one of the first impedance-modifying fluid and the second impedance-modifying fluid to change the mixture during at least one of before and during a delivery of energy from the energy delivery device.

In one embodiment, a method for ablating tissue comprises delivering an impedance-modifying fluid to a treatment site and delivering pulsed field ablation energy to the treatment site.

In one aspect of the embodiment, the treatment site includes an area of target tissue and blood in contact with the area of target tissue, the pulsed field ablation energy being delivered to the area of target tissue and the impedance-modifying fluid being delivered to the blood.

In one aspect of the embodiment, the impedance-modifying fluid is delivered to the blood immediately before the pulsed field ablation energy is delivered to the area of target tissue.

In one aspect of the embodiment, the impedance-modifying fluid is delivered to the blood simultaneously with the delivery of pulsed field ablation energy to the area of target tissue.

In one aspect of the embodiment, the treatment site includes an area of epicardial tissue and a pericardial space in contact with the area of epicardial tissue, the pulsed filed ablation energy being delivered to the area of epicardial tissue and the impedance-modifying fluid being delivered to the pericardial space.

In one embodiment, a tissue ablation device comprises: an elongate body having a distal portion and a proximal portion opposite the distal portion, the distal portion including a distal end; an energy delivery electrode at the distal portion of the elongate body; an energy return electrode on the elongate body proximal to the energy delivery electrode, the energy return electrode having a first outer diameter; and a distancing element on the elongate body proximate the energy return electrode, the distancing element having a second outer diameter that is greater than the first outer diameter.

In one aspect of the embodiment, the distancing element is composed of a non-conductive material.

In one aspect of the embodiment, the distancing element is at least one of a fin, a ring, and a spline.

In one aspect of the embodiment, the distancing element is transitionable between a delivery configuration and an expanded configuration, the distancing element having the second outer diameter when the distancing element is in the expanded configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
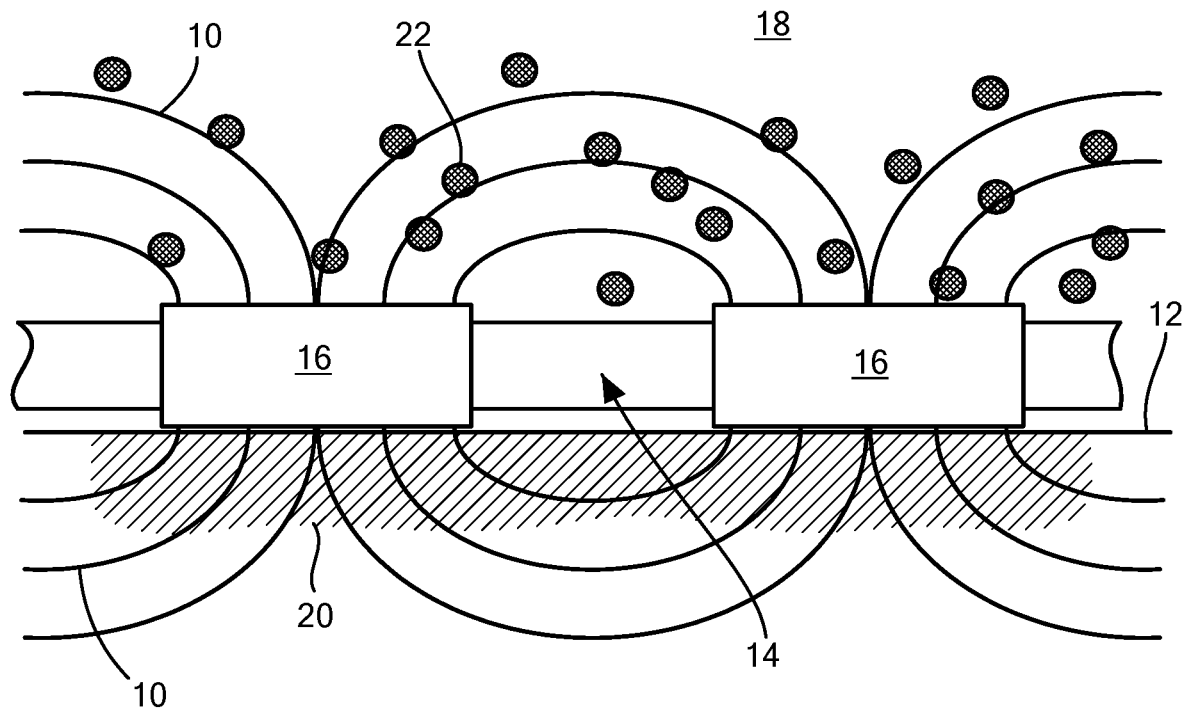
FIG. 1 shows an exemplary delivery of pulsed field ablation energy to tissue as known in the art.

Before describing in detail exemplary embodiments, it is noted that the embodiments reside primarily in combinations of apparatus components and processing steps related to ablating tissue. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, the terms "pulsed field ablation" (PFA) or "pulsed field ablation energy" refer to a form of electrical energy delivery that produces tissue lesions through the mechanism of irreversible electroporation (IRE). The electric field gradient produced by application of high voltage to individual or multiple electrodes surrounds those electrode(s) to some extent beyond the dimensions of those electrode(s), penetrating into surrounding tissues to disrupt cell membranes through the process of IRE. Tissues exposed to a PFA electric field gradient at or above the threshold for IRE will form lesions, while tissues exposed to less than the IRE threshold field gradient will survive. Such PFA deliveries are desired to produce high electric field gradients with a minimum of electrical current, such that the current delivered is not sufficient to induce significant generation of heat within the surrounding tissues. The devices, systems, and methods disclosed herein minimize excess electrical current delivered during applications of high-voltage PFA.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 2:
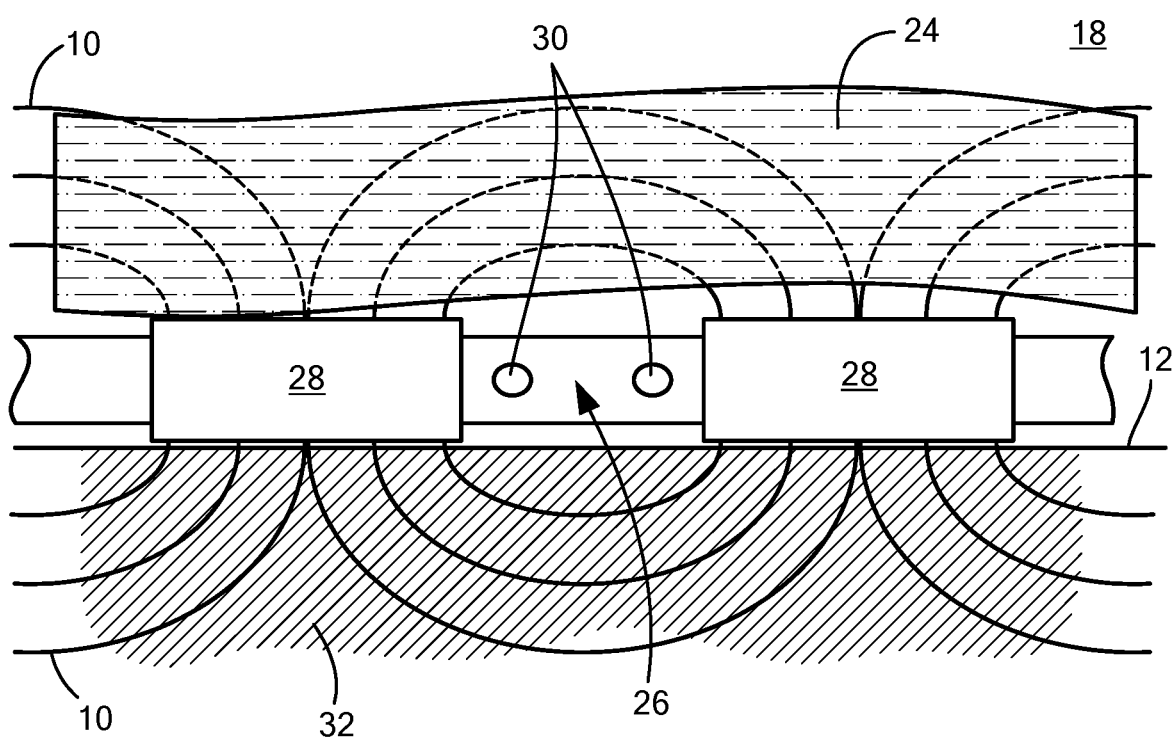
FIG. 2 shows an exemplary delivery of pulsed field ablation energy with an impedance-modifying fluid.

Referring now to FIGS. 1 and 2, exemplary deliveries of pulsed field ablation energy are shown. FIG. 1 shows the delivery of pulsed field ablation energy 10 to an area of tissue 12 as is known in the art. Specifically, at least a portion of a medical device 14, such as a portion of an energy delivery device 14 including one or more electrodes 16, is placed proximate or in contact with an area of tissue 12. Pulsed field ablation energy 10 is delivered from the electrode(s) 16 to the tissue 12, but is also delivered toward the blood 18 surrounding the tissue. Whereas delivery of pulsed field ablation energy 10 to the tissue 12 causes an ablation lesion 20, delivery of pulsed field ablation energy 10 to the blood 18 may cause the formation of gas bubbles, hemolysis, and/or thermally denatured blood proteins 22.

In contrast, FIG. 2 shows the delivery of pulsed field ablation energy 10 to an area of tissue 12, with an impedance-modifying fluid 24. As in the delivery of FIG. 1, at least a portion of a medical device 26, such as a portion of an energy delivery device 26 including one or more electrodes 28, is placed proximate or in contact with an area of tissue 12. However, immediately before and/or during the delivery of pulsed field ablation energy 10, a bolus or volume of impedance-modifying fluid 24 is injected from one or more irrigation ports 30 in the energy delivery device 26. In one embodiment, the impedance-modifying fluid 24 is a hypotonic fluid that briefly raises the electrical impedance of the blood 18 environment surrounding the electrode(s) 28 to a level that reduces the electrical current delivered through the blood 18, thereby reducing or eliminating local heating of the blood. By reducing the current delivered to the blood, the current density of the non-blood (i.e. tissue) side of an electrode 28 may be slightly higher, as there is less electrode surface area through which the voltage is driving current. Thus, current that would otherwise be delivered to the blood (wasted current) is minimized, thereby allowing most of the current to be directed to the myocardium, the intended ablation target. This may also limit the total amount of hemolysis in the blood, bubbles generated by electrolysis, and/or coagulation of the blood, even during the creation of deep lesions. Additionally, the use of the impedance-modifying fluid 24 helps focus the pulsed field ablation energy 10 toward only the target tissue 12 and results in more effective lesion formation and/or the formation of deeper lesions 36 than lesions 34 created using techniques that do not use the impedance-modifying fluid 24. This delivery of impedance-modifying fluid 24 immediately before and/or during a delivery of pulsed field ablation energy 10 may be particularly useful when delivering a series of rapid high voltage pulses. However, the method is not limited to pulsed field ablation, as it may also offer advantages when delivering conventional radiofrequency energy for hyperthermal ablation of tissue. In another embodiment, however, the impedance-modifying fluid 24 is hypertonic fluid that briefly reduces the electrical impedance of the blood 18 environment surrounding the electrode(s) 28 to a level that increases the electrical current delivered through the blood 18. Alternatively, both a hypotonic fluid and a hypertonic fluid may be used.

Figure 3:
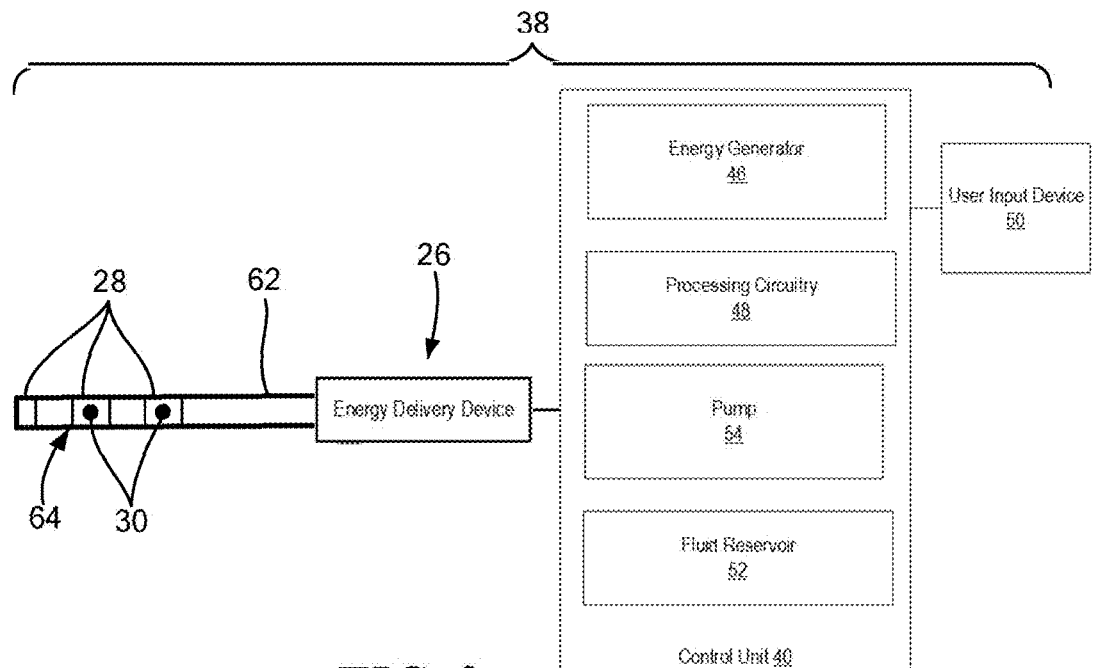
FIG. 3 shows an exemplary medical system for delivering pulsed field ablation energy with an impedance-modifying fluid.
Figure 13:
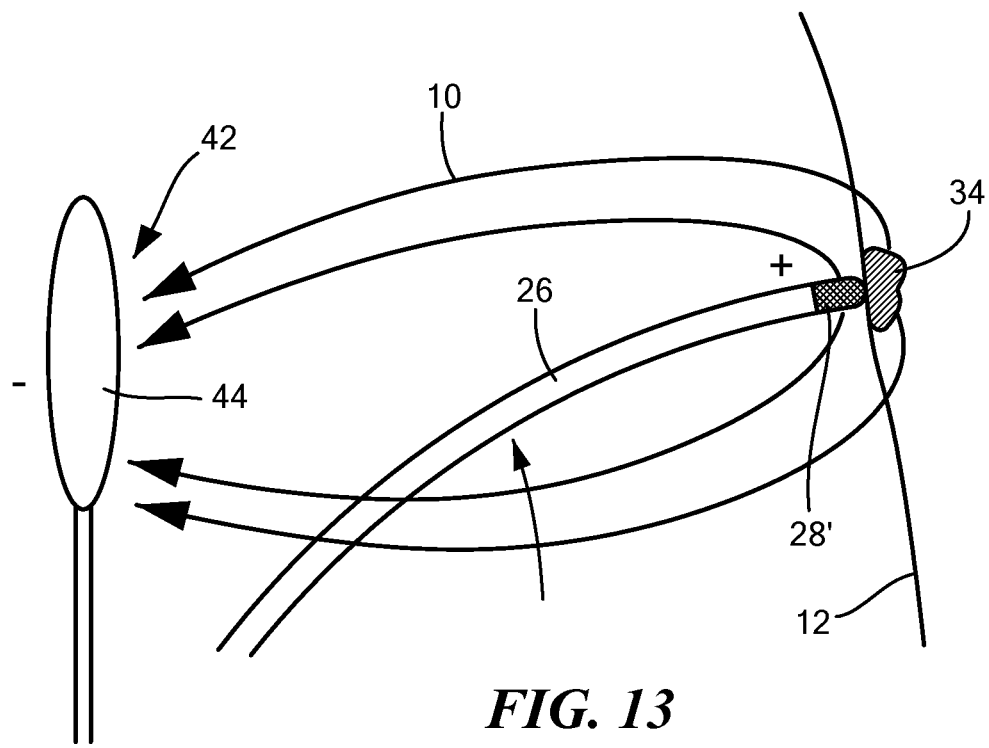
FIG. 13 shows treatment of tissue using an energy delivery device, such as a pulsed field ablation device, and an energy return electrode as known in the art.
Figure 14:
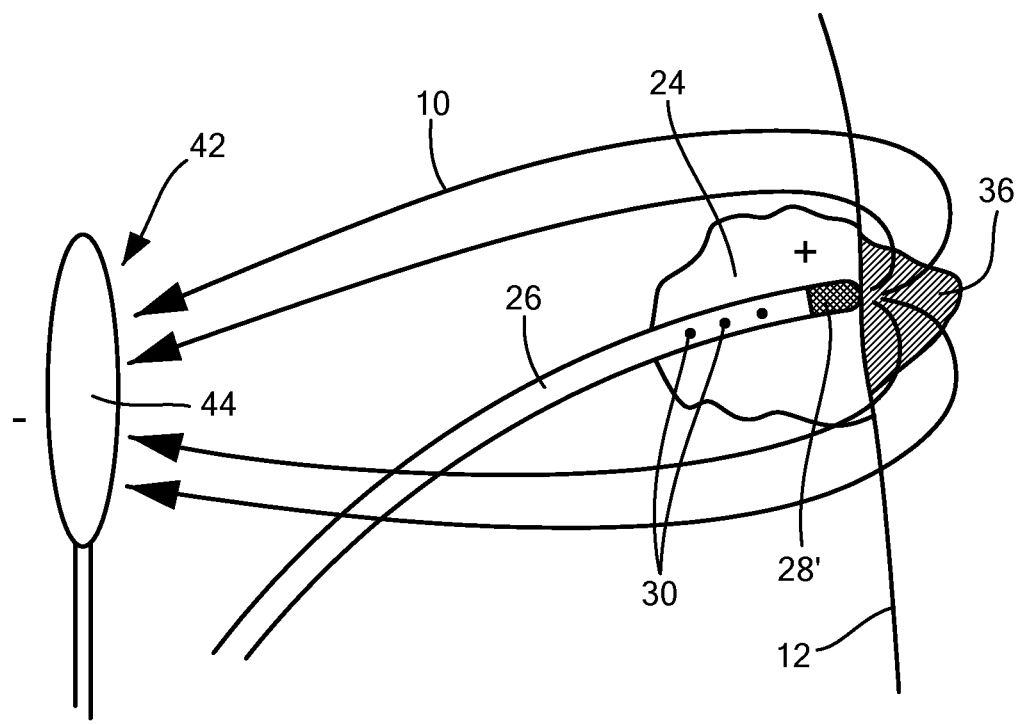
FIG. 14 shows a treatment of tissue using an energy delivery device, such as a pulsed field ablation device, and an energy return electrode, with the use of an impedance-modifying fluid.

Referring now to FIG. 3, an exemplary medical system for delivering pulsed field ablation energy with an impedance-modifying fluid is shown. In one embodiment, the medical system 38 generally includes a medical device 26, such as an energy delivery device 26, having one or more electrodes 28 and one or more irrigation ports 30, and a control unit 40 in communication with the energy delivery device 26. The energy delivery device 26 may be used to deliver both impedance-modifying fluid 24 and pulsed field ablation energy 10 (and/or other types of energy or thermal treatments). The medical system 38 may additionally include one or more secondary devices 42, such as a secondary device 42 having one or more energy return electrodes 44 (for example, as shown in FIGS. 13 and 14).

The control unit 40 includes one or more system components for the delivery, control, and monitoring of ablation energy and impedance-modifying fluid 24. The control unit 40 may be configured for use with one or more ablation energy modalities in addition to non-thermal pulsed field ablation, such as radiofrequency ablation, laser ablation, microwave ablation, cryoablation, or the like. In one embodiment, the control unit 40 includes an energy generator 46 for the delivery of pulsed field ablation energy 10 for the irreversible and/or reversible electroporation of tissue 12. The energy generator 46 is in communication with the energy delivery device 26 such that energy is delivered from the energy generator 46 through the one or more electrodes 28. The control unit 40 may further include one or more controllers, processors, and/or software modules containing instructions or algorithms to provide for the automated operation and performance of the features, sequences, or procedures described herein. In one embodiment, for example, the control unit 40 includes processing circuitry 48 with a memory and a processor. The memory is in electrical communication with the processor and includes instructions that, when executed by the processor, configure the processor to receive, process, or otherwise use signals from the energy delivery device and/or other system components. The processing circuitry 48 may further include at least one timing circuit for controlling the delivery of the impedance-modifying fluid 24 (for example, timing the delivery of the impedance-modifying fluid 24 relative to the delivery of pulsed field ablation energy 10). Still further, the control unit 40 may include one or more user input devices, controllers, and/or displays (which may each generally be referred to as a user input device 50 for simplicity) for collecting and conveying information from and to the user.

The medical system 38 is configured to deliver at least irreversible electroporation energy (pulsed field ablation energy), and may optionally be configured for use with other energy modalities as well, such as laser ablation, irreversible electroporation, cryoablation, microwave ablation, thermal radiofrequency ablation, or the like. Electroporation is a phenomenon causing cell membranes to become "leaky" (that is, permeable for molecules for which the cell membrane may otherwise be impermeable or semipermeable). Electroporation, which may also be referred to as electropermeabilization, pulsed electric field treatment, non-thermal irreversible electroporation, irreversible electroporation, high frequency irreversible electroporation, nanosecond electroporation, or nanoelectroporation, involves the application of high-amplitude pulses to cause physiological modification (i.e., permeabilization) of the cells of the tissue to which the energy is applied. These pulses preferably may be short (for example, nanosecond, microsecond, or millisecond pulse width) in order to allow the application of high voltage, high current (for example, 20 or more amps) without long duration(s) of electrical current flow that may otherwise cause significant tissue heating and muscle stimulation. The pulsed electric energy may induce the formation of microscopic defects that result in hyperpermeabilization of the cell membrane. Depending on the characteristics of the electrical pulses, an electroporated cell can survive electroporation, referred to as "reversible electroporation," or die, referred to as "irreversible electroporation" (IRE). Reversible electroporation may be used to transfer agents, including genetic material and other large or small molecules, into targeted cells for various purposes, including the alteration of the action potentials of cardiac myocytes.

The energy generator 46 may provide electrical pulses to the energy delivery device 26 to perform an electroporation procedure to cardiac tissue or other tissues within the patient's body, such as renal tissue, airway tissue, and organs or tissue within the cardiac space or the pericardial space. Specifically, the energy generator 46 may be configured and programmed to deliver pulsed, high-voltage electric fields appropriate for achieving desired pulsed, high-voltage ablation (referred to as "pulsed field ablation" or "pulsed electric field ablation") and/or pulsed radiofrequency ablation. As a point of reference, the non-radiofrequency pulsed high-voltage ablation effects of the present disclosure are distinguishable from DC current ablation, as well as thermally-induced ablation attendant with conventional RF techniques. For example, the pulse trains delivered by the energy generator may be delivered at a frequency less than 30 kHz, and in an exemplary configuration, 1 kHz, which is a lower frequency than radiofrequency treatments. The pulsed-field energy in accordance with the present disclosure may be sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals. Additionally or alternatively, the energy generator may be configured and programmed to deliver RF energy appropriate for achieving tissue ablation.

Although not shown, the medical system 38 may include one or more sensors to monitor the operating parameters through the medical system 38, such as pressure, temperature, delivered voltage, or the like, and for measuring and monitoring one or more tissue characteristics, such as EGM waveforms, monophasic action potentials, tissue impedance, or the like, in addition to monitoring, recording, or otherwise conveying measurements or conditions within the energy delivery device 26 or other component of the medical system 38 or the ambient environment at the distal portion of the energy delivery device 26. The sensor(s) may be in communication with the control unit 40 for initiating or triggering one or more alerts or ablation energy delivery modifications during operation of the energy delivery device 26.

In one embodiment, the control unit 40 also includes at least one fluid reservoir 52 containing at least one impedance-modifying fluid 24 and at least one pump 54 for delivering the impedance-modifying fluid 24 before and/or during the delivery of pulsed field ablation energy 10. In one embodiment, the at least one impedance-modifying fluid 24 is a hypotonic (low ionic strength) fluid to direct electrical fields during ablation, such as 0.25% saline, 0.45% saline and/or glucose, Dextran-40, Dextran-70, 2.5% dextrose solution, glucose solution, or the like. Optionally, the at least one impedance-modifying fluid 24 may be chosen such that it matches or reasonably approximates the osmolality of blood. The at least one pump 54 is in communication with the processing circuitry 48 of the control unit 40, and the processing circuitry 48 controls the timing and delivery of the impedance-modifying fluid 24 relative based on the delivery of the pulsed field ablation energy 10. In one embodiment, the processing circuitry 48 is configured to time the delivery of the impedance-modifying fluid 24 relative to a delivery of pulsed field ablation energy 10, such that the processing circuitry 48 instructs the pump 54 to deliver a bolus or volume of the impedance-modifying fluid 24 from the irrigation port(s) 30 of the energy delivery device 26 immediately before and/or during the delivery of pulsed field ablation energy 10. In one embodiment, the processing circuitry 48 instructs the pump 54 to deliver the impedance-modifying fluid 24 between approximately one second and approximately three seconds before the onset of the delivery of pulsed field ablation energy 10. Additionally or alternatively, the processing circuitry 48 instructs the pump 54 to deliver the impedance-modifying fluid 24 during the delivery of pulsed field ablation energy 10. In one embodiment, delivery of impedance-modifying fluid 24 is halted immediately upon completion of pulsed field ablation energy delivery.

In one embodiment, the control unit 40 is configured to deliver one or more test pulses or deliver high-frequency continuous signals from the electrode(s) 28 of the energy delivery device 26 to measure the impedance at the electrode(s) 28 after the delivery of impedance-modifying fluid 24 and before the delivery of pulsed field ablation energy 10 to verify that the impedance of the blood-tissue environment 18/12 surrounding the electrode(s) 28 has been altered by a desired about to enhance lesion formation and limit the formation of emboli such as gas bubbles and/or thermally denatured blood proteins 22. If the control unit 40 (for example, the processing circuitry 48) determines the impedance of the blood-tissue environment 18/12 has been adequately altered, the control unit 40 will instruct the energy generator 46 to deliver pulsed field ablation energy 10 from the electrode(s) 28. If, on the other hand, the control unit 40 determines the impedance of the blood-tissue environment 18/12 has not been adequately altered, the control unit 40 will instruct the pump 54 to deliver another bolus or volume of impedance-modifying fluid 24. In this case, the control unit 40 will delivery one or more further test pulses before the initiation of delivery of pulsed field ablation energy 10 from the energy generator 46.

The control unit 40 may optionally include at least one fluid recovery reservoir (not shown) for the collection of recovered impedance-modifying fluid from the treatment site(s). In this embodiment, the control unit 40 also includes one or more system components for the removal of fluid and/or other particles from the treatment site. In one embodiment, the control unit 40 includes a fluid removal component (not shown), such as a vacuum pump, syringe pump, or vacuum containers that exert suction on one or more fluid evacuation conduits of the energy delivery device 26 (disclosed in more detail below).

Figure 4:
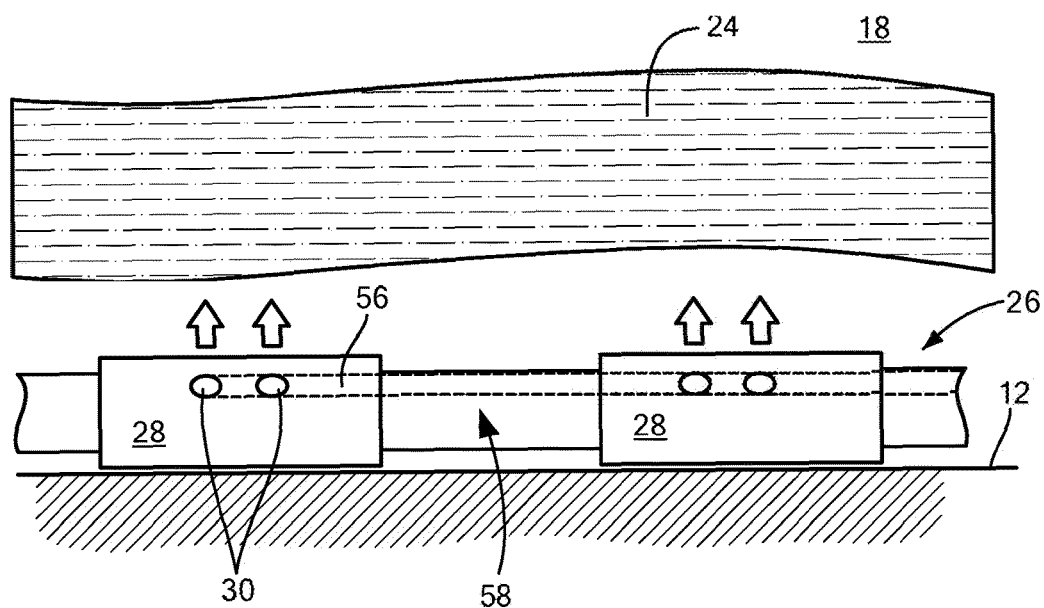
FIG. 4 shows a first configuration of a portion of a medical device for delivering pulsed field ablation energy and impedance-modifying fluid.
Figure 5:
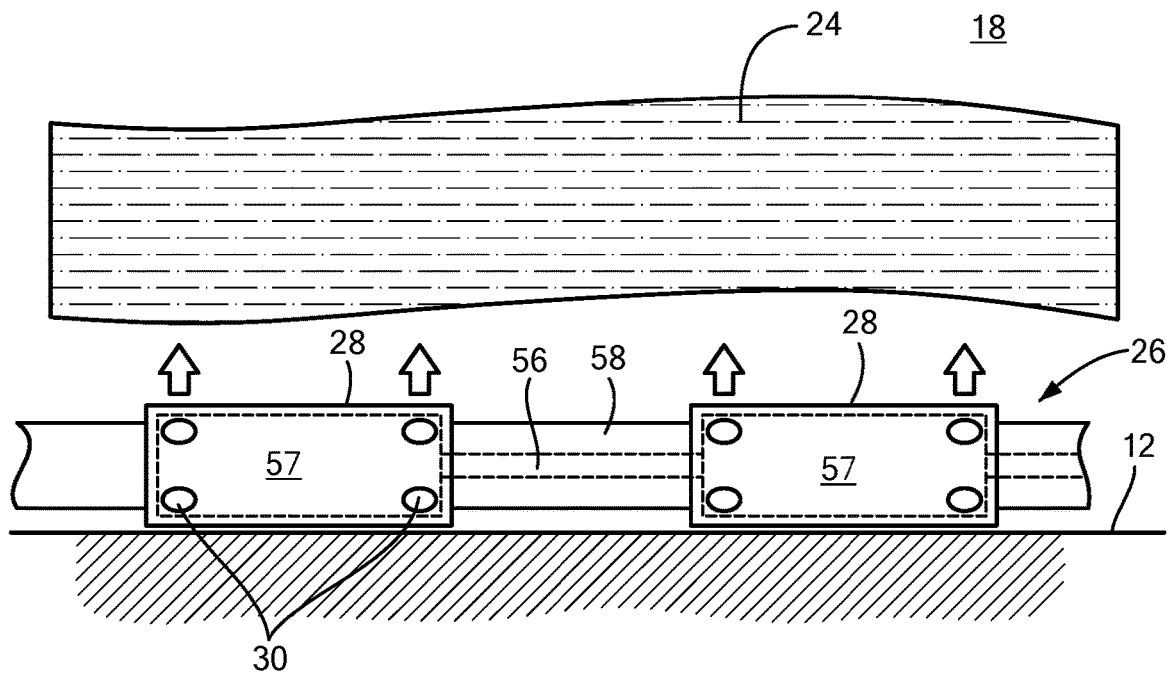
FIG. 5 shows a second configuration of a portion of a medical device for delivering pulsed field ablation energy and impedance-modifying fluid.
Figure 6:
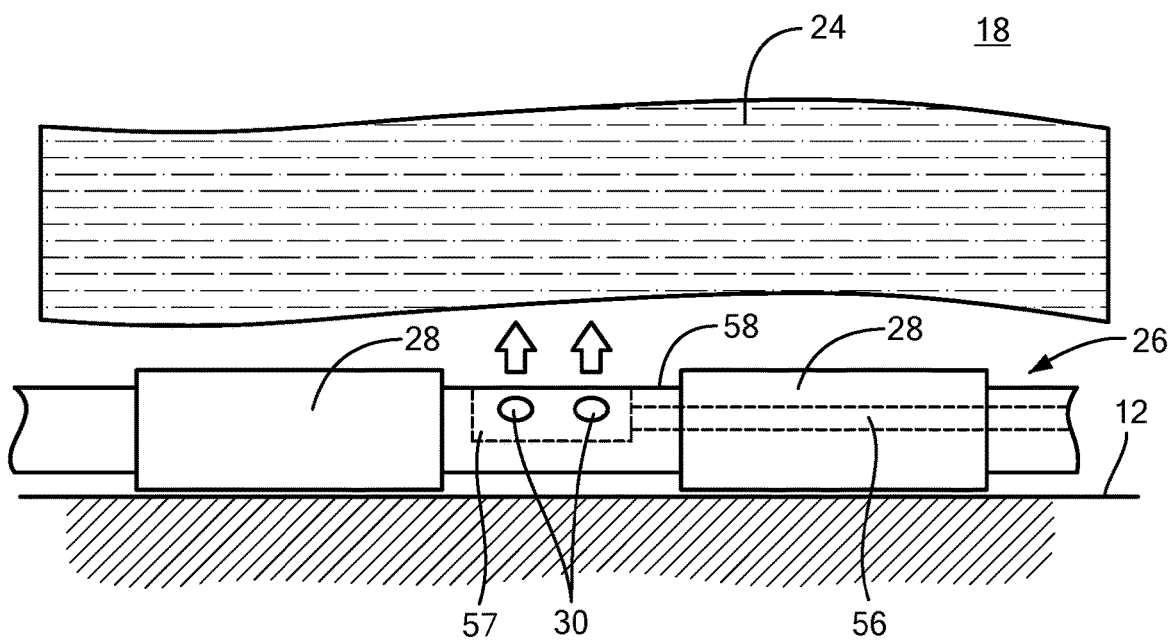
FIG. 6 shows a third configuration of a portion of a medical device for delivering pulsed field ablation energy and impedance-modifying fluid.

Referring now to FIGS. 4-10, embodiments of an energy delivery device 26 for delivering pulsed field ablation energy 10 and impedance-modifying fluid 24 are shown. In general, each of the embodiments of FIGS. 4-10 includes an energy delivery device 26 having at least one electrode 28 and at least one irrigation port 30. The energy delivery device 26 may be a focal catheter with an elongate body having one or more electrodes 28. Alternatively, the energy delivery device 26 may have any other suitable configuration, including, but not limited to, a device having an expandable treatment element with an electrode array. The electrode(s) 28 are in electrical communication with the control unit 40 (for example, the energy generator 46 and the processing circuitry 48) for the delivery of pulsed field ablation energy 10. The irrigation port(s) 30 are in fluid communication with the at least one fluid reservoir 52 through at least one fluid delivery conduit 56 (for example, as shown in FIG. 4). The irrigation port(s) 30 may be located on the energy delivery device 26 such that the irrigation port(s) 30 are oriented away from the target tissue (that is, face the blood 18) when the electrode(s) 28 are in contact with the target tissue. Additionally or alternatively, the irrigation port(s) 30 are selectively operable such that the control unit 40 and/or the user may select from which port(s) 30 to deliver the impedance-modifying fluid 24. Thus, delivery of the impedance-modifying fluid 24 may create a cloud or volume of impedance-modifying fluid 24 opposite the location of electrode-tissue contact, thereby driving the electrical current away from the impedance-modifying fluid 24 and toward the target tissue 12. In a similar manner, a delivery of impedance-modifying fluid 24 (such as hypotonic impedance-modifying fluid) may be injected from the irrigation ports 30 into the pericardial space when the electrode(s) 28 are located within the pericardial space and in contact with the epicardial surface of the heart, thereby driving current into the epicardium of the heart and minimizing current passing into the pericardium and away from the heart. The irrigation port(s) 30 may be designed with an internal fluid manifold of larger diameter than the more proximal fluid delivery lumens, such that relatively low pressure is exerted by the fluid exiting the electrode(s) 28, thus avoiding the fluid being forced out of the irrigation port(s) 30 that may be occluded by tissue contact. In one embodiment, the energy delivery device 26 includes one or more chambers 57 within the elongate body and in fluid communication with the fluid delivery conduit 56 and the irrigation port(s) 30, each chamber 57 proximate one or more energy delivery electrode(s) 28 (for example, as shown in FIGS. 5 and 6). In one embodiment, each chamber 57 provides an increased volume over the fluid delivery conduit 56. Such a configuration ensures that the electrode(s) 28 will remain in firm tissue contact while the impedance-modifying fluid exits the electrode(s) 28 on the tissue-contacting side(s). For example, it is desired that the electrode(s) 28 remain in firm contact with the tissue to be ablated; however, high-pressure jets of impedance-modifying fluid 24 may lift the electrode(s) 28 out of tissue contact and/or form a layer of low conductivity fluid between the electrode(s) 28 and the targeted tissue.

Optionally, at least some of the irrigation port(s) 30 are in fluid communication with the at least one fluid recovery reservoir and fluid removal component through at least one fluid evacuation conduit (not shown, although it will be understood that the at least one fluid delivery conduit 56 may additionally or alternatively function as the at least one fluid evacuation conduit). In one embodiment, each irrigation port 30 selectively may be used for either delivery or evacuation of impedance-modifying fluid 24, and the control unit 40 may be configured to automatically or semi-automatically selectively connect each of the irrigation port(s) 30 to the pump 54 and fluid reservoir(s) 52 or the fluid removal component and the fluid recovery reservoir(s). Additionally or alternatively, the user may manually control the function of each irrigation port 30 (that is, whether each irrigation port 30 is used for fluid delivery or fluid evacuation). For simplicity, the energy delivery devices 26 shown in the figures are hereinafter described as having irrigation ports 30 for the delivery of impedance-modifying fluid 24, although it will be understood that each irrigation port 30 may additionally or alternatively be used for fluid evacuation. Exemplary configurations of the irrigation port(s) 30 are shown in FIGS. 4-10; however, the irrigation port(s) 30 are not limited to the configurations shown, and may have any suitable size, shape, distribution pattern, location, or other characteristics.

Referring to FIG. 4, the energy delivery device 26 includes an elongate body, shaft, carrier arm, or other structure 58 bearing at least one electrode 28 for delivering pulsed field ablation energy 10. Each electrode 28 includes at least one irrigation port 30 for the delivery of impedance-modifying fluid 24. In one embodiment, each irrigation port 30 is in fluid communication with the at least one fluid reservoir 52 through a fluid delivery conduit 56. Referring to FIG. 5, the energy delivery device 26 is similar to that of FIG. 4, but includes the at least one irrigation port 30 on or proximate the edges of the electrode(s) 28. In one embodiment, the at least one irrigation port 30 is immediately proximate at least one edge of the electrode 28, such as within 0.5 mm. The electric fields delivered by the electrode(s) 28 can be highly concentrated in these areas, and are therefore desirable targets for minimizing the electrical current. The increase in blood impedance surrounding the electrode(s) 28 produced by the delivery of the impedance-modifying fluid 24, such as a hypotonic fluid, lowers that overall current delivered while maintaining current through the side of each electrode 28 that is in direct contact with the targeted tissue 12, which has a lower impedance path. Thus, the electric current is steered or directed toward target tissue 12 and away from the blood 18 and non-target tissue. Additionally, the formation of gas bubbles and/or char is minimized or prevented without the need for continuous irrigation throughout the duration of energy delivery.

Referring to FIG. 6, the energy delivery device 26 includes an elongate body, shaft, carrier arm, or other structure 58 bearing at least one electrode 28 for the delivery of pulsed field ablation energy 10. In contrast to the embodiments shown in FIGS. 4 and 5, the embodiment shown in FIG. 6 includes at least one irrigation port 30 in the electrode-bearing structure 58 rather than on the electrode(s) 28 themselves. In one embodiment, each irrigation port 30 is in fluid communication with the at least one fluid reservoir 52 through a fluid delivery conduit 56.

Figure 7:
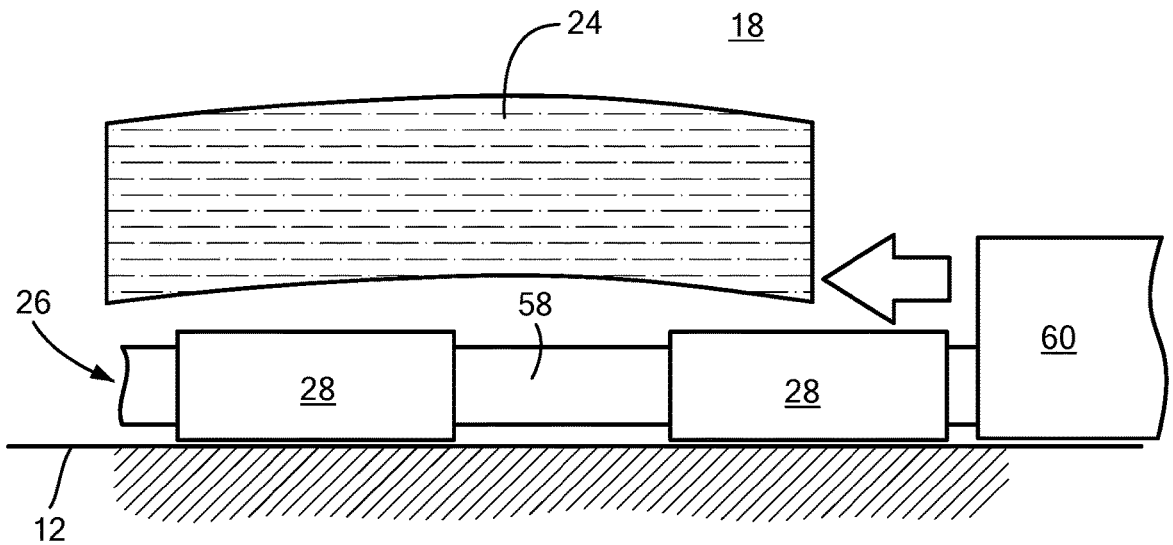
FIG. 7 shows a fourth configuration of a portion of a medical device for delivering pulsed field ablation energy and impedance-modifying fluid.
Figure 8:
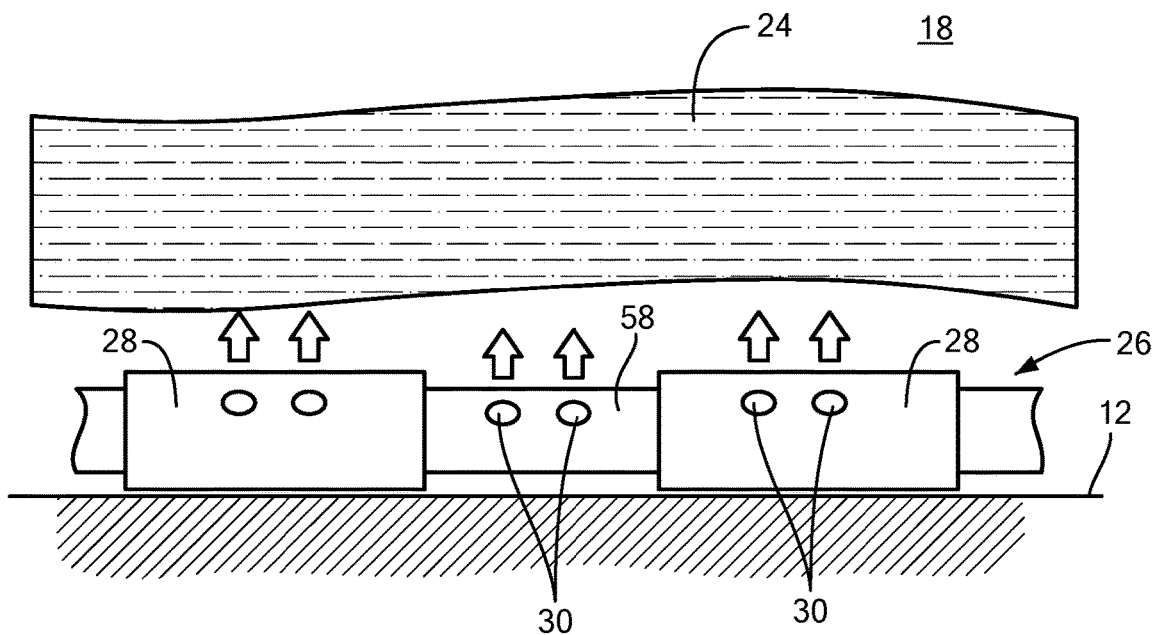
FIG. 8 shows a fifth configuration of a portion of a medical device for delivering pulsed field ablation energy and impedance-modifying fluid.

Referring to FIG. 7, the impedance-modifying fluid 24 is delivered from a device other than directly from the energy delivery device 26. In one embodiment, the impedance-modifying fluid 24 is delivered to the treatment site through a delivery sheath 60 for the energy delivery device 26. Additionally or alternatively, the impedance-modifying fluid 24 may be delivered to the treatment site through a secondary device (not shown in FIG. 7), such as a secondary sheath or secondary medical device.

Figure 9:
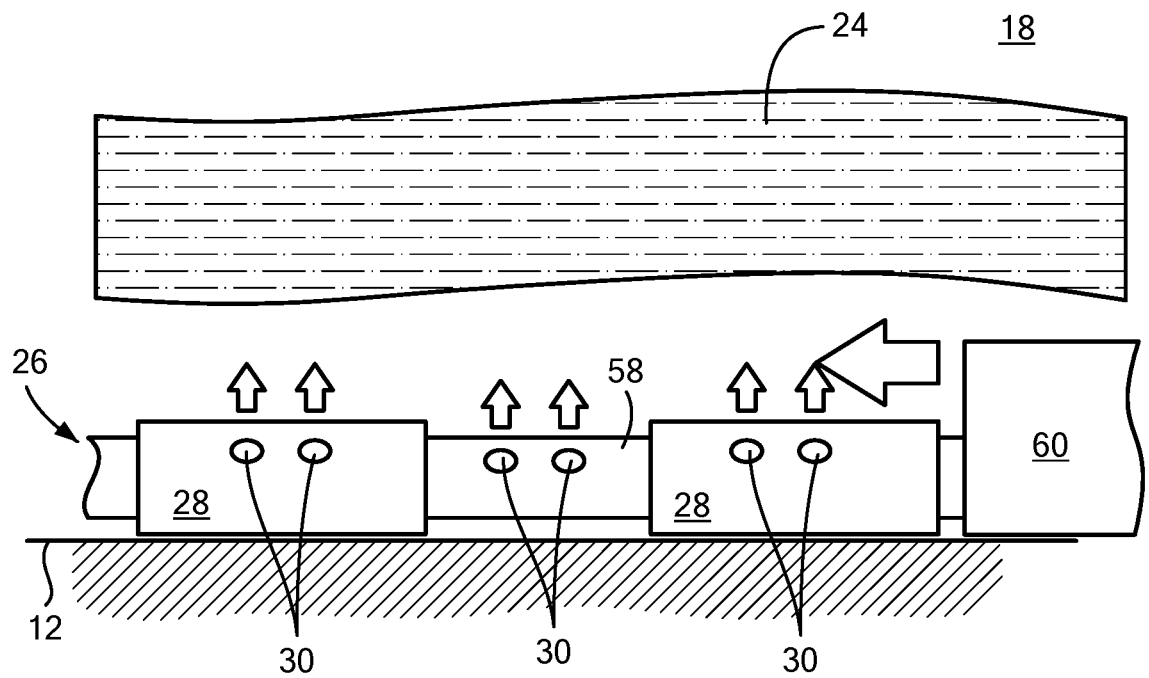
FIG. 9 shows a sixth configuration of a portion of a medical device for delivering pulsed field ablation energy and impedance-modifying fluid.
Figure 10:
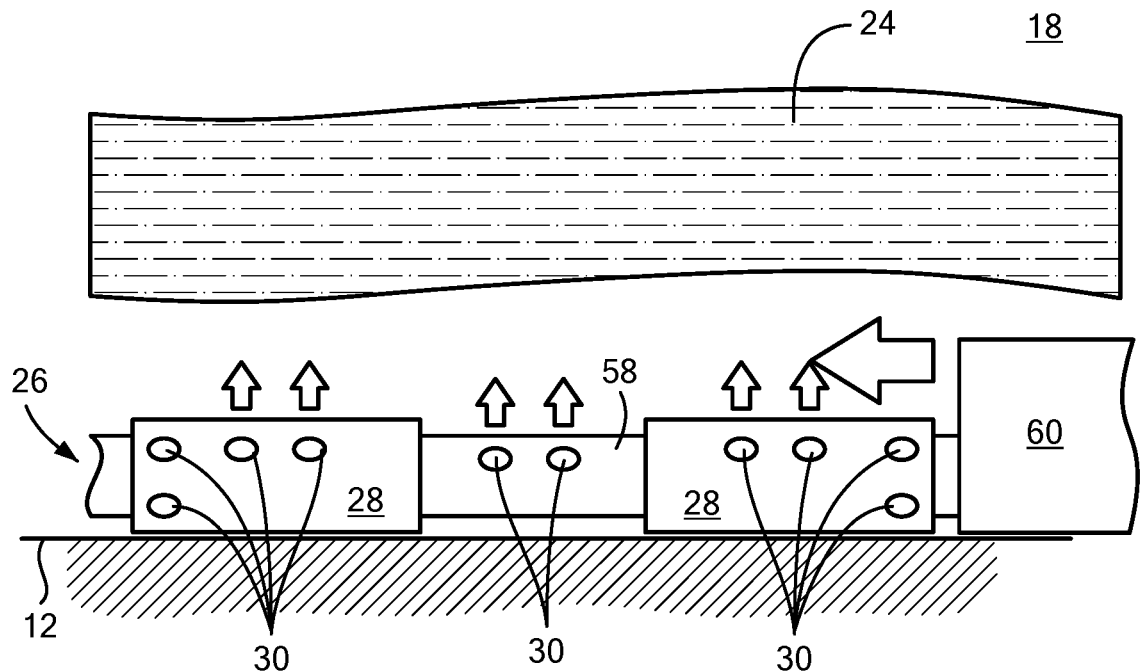
FIG. 10 shows a seventh configuration of a portion of a medical device for delivering pulsed field ablation energy and impedance-modifying fluid.

However, it will be understood that combinations of the above may also be used. For example, referring to FIG. 8, the energy delivery device 26 includes a combination of irrigation port(s) 30 in at least one electrode 28 and irrigation port(s) 30 in the electrode-bearing structure 58. Alternatively, the energy delivery device 26 shown in FIG. 8 may additionally be used to deliver impedance-modifying fluid 24 from the delivery sheath 60 and/or from a secondary device, as shown in FIG. 9. In another embodiment, shown in FIG. 10, the energy delivery device 26 includes a combination of irrigation port(s) 30 at or proximate the edge of the at least one electrode 28 and irrigation port(s) 30 in the electrode-bearing structure 58, as well as a delivery sheath 60 and/or secondary device for delivering the impedance-modifying fluid 24. Further, other embodiment and combinations not shown herein are also contemplated for the delivery of impedance-modifying fluid 24 to the treatment site.

Figure 11:
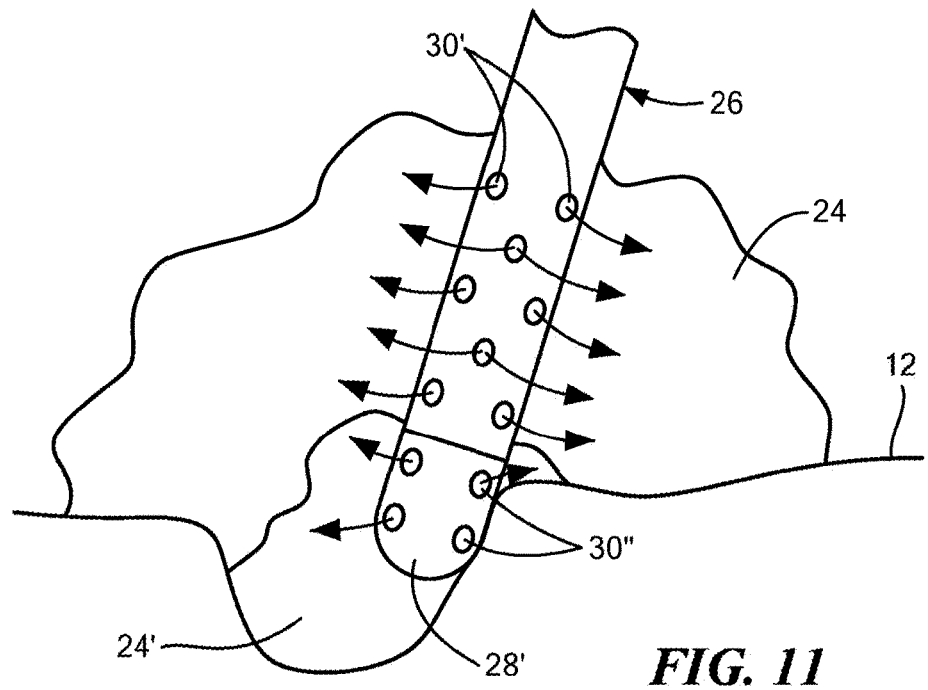
FIG. 11 shows a portion of a medical device ablating tissue using pulsed field ablation energy and delivering a first impedance-modifying fluid and a second impedance-modifying fluid.
Figure 12:
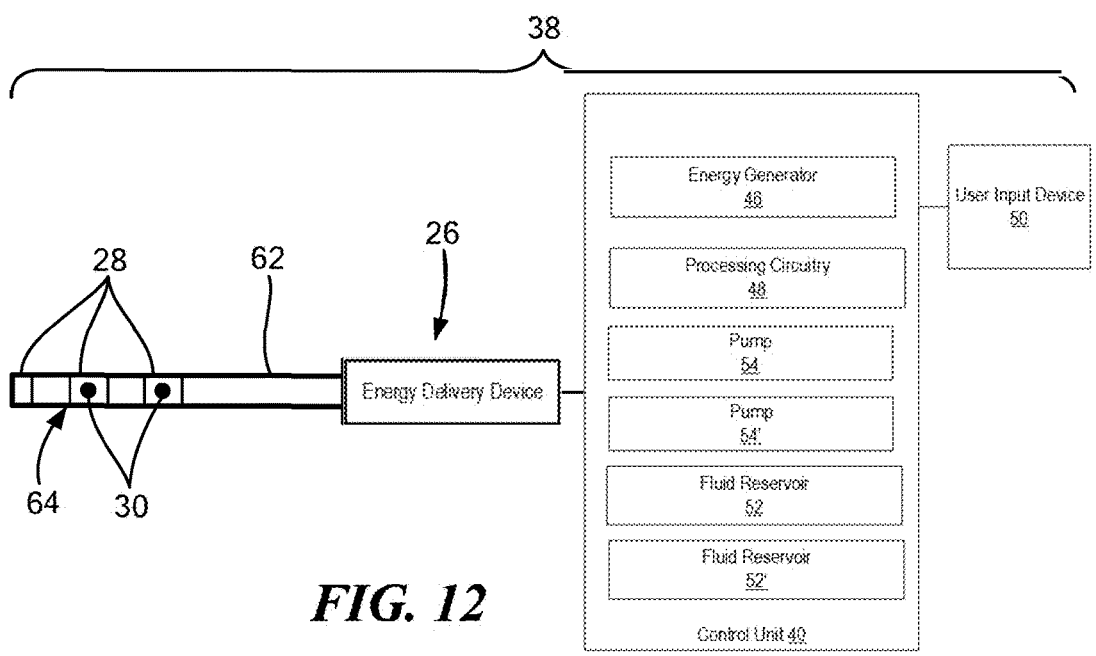
FIG. 12 shows an exemplary medical system for use with the device of FIG. 12, the medical system including a first fluid reservoir containing a first impedance-modifying fluid and a second fluid reservoir containing a second impedance-modifying fluid.

Referring now to FIG. 11, a portion of an energy delivery device 26 ablating tissue 12 using pulsed field ablation energy and delivering a first impedance-modifying fluid 24 and a second impedance-modifying fluid 24' is shown. As discussed above, a hypotonic impedance-modifying fluid will, at least temporarily, increase the impedance of the blood environment surrounding the electrode(s) to a level that reduces the electrical current being delivered through the blood 18, thereby reducing or eliminating local heating generated by high current densities and helping to direct the electrical current toward and into the target tissue 12. However, the medical system 38 may include at least a first fluid reservoir 52 and a second fluid reservoir 52' (which may optionally be in fluid communication with a second pump 54'), each of which containing a different impedance-modifying fluid (24, 24', respectively). An exemplary medical system 38 for delivering a first 24 and a second 24' impedance-modifying fluid is shown in FIG. 12. The medical system 38 of FIG. 12 is similar to the medical system 38 of FIG. 3, but includes a first fluid reservoir 52 and a second fluid reservoir 52'.

In one embodiment, the energy delivery device 26 of FIG. 11 may be used to deliver a first impedance-modifying fluid 24 (for example, from the first fluid reservoir 52) that is a hypotonic fluid from a first one or more irrigation ports 30 located proximal to a distal tip or distal electrode 28' of the energy delivery device 26. For example, the first one or more irrigation ports 30 includes a first plurality of irrigation ports 30'. This hypotonic fluid 24 helps insulate the blood 18 and non-target tissue to reduce the occurrence of gas bubbles and thermally denatured protein formation, and also drives the electrical current toward and into the target tissue 12. The energy delivery device 26 is also used to deliver a second impedance-modifying fluid 24' (for example, from the second fluid reservoir 52') from a second one or more irrigation ports 30" located at or proximate the distal tip or distal electrode 28' of the energy delivery device. For example, the second one or more irrigation ports 30" includes a second plurality of irrigation ports 30", which may be sized and configured similar to the first plurality of irrigation ports 30. In one embodiment, the second impedance-modifying fluid 24' is a hypertonic fluid, such as a fluid with a higher concentration of sodium chloride (for example, a hypertonic solution containing 2%, 3%, 5%, or 7% sodium chloride by weight), or a fluid that includes ions that act as an adjuvant to increase the lethality of the electric field (for example, solutions containing calcium, such as calcium gluconate or calcium chloride). The second impedance-modifying fluid 24' will, at least temporarily, decrease the impedance of the blood environment surrounding the electrode(s) 28 to a level that increases the electrical current being delivered through the area of the first impedance-modifying fluid 24 as the electrical current approaches the target tissue 12, thereby enhancing lesion formation and filling in any gaps in lesion formation in non-uniform tissue. In one embodiment, the second plurality of irrigation ports 30" includes fewer irrigation ports 30" than the first plurality of irrigation ports 30', and/or each of the first plurality of irrigation ports 30' has a larger aperture size (diameter) than each of the second plurality of irrigation ports 30", such that a greater amount of hypotonic first impedance-modifying fluid 24 is delivered to the treatment site 12 than the hypertonic second impedance-modifying fluid 24'. Further, the first 24 and second 24' impedance-modifying fluids may be delivered in short bursts during or between deliveries of bursts or pulses of pulsed field ablation energy, so that an amount of each impedance-modifying fluid 24, 24' is maintained at the desired locations (for example, so that the hypotonic first impedance-modifying fluid 24 is maintained at a location farther from the target tissue 12 than the hypertonic second impedance-modifying fluid 24'). Optionally, the first 24 and second 24' impedance-modifying fluids may be delivered from the same irrigation port(s) 30, and the control unit 40 (for example, the processing circuitry 48) may be configured to automatically or semi-automatically, or accept user input to, modify the relative concentrations of the impedance-modifying fluids 24, 24' to have a greater control over the depth, even over a limited set of ablation parameter choices. In one non-limiting example, the impedance-modifying fluid mixture may be modified from a 20% hypertonic fluid/80% hypotonic fluid solution (which may result in the creation of a shallower lesion) to a 100% hypotonic fluid (which may result in the creation of a deeper lesion).

Alternatively, the energy delivery device 26 of FIG. 11 may be used to deliver only a hypertonic fluid from the one or more irrigation ports 30, rather than only a hypotonic fluid or both hypertonic and hypotonic fluids. This hypertonic fluid 24 helps spread the electric field through complex anatomy, such that the effect of tissue contact is minimized. The hypertonic fluid also expands the effective surface area of each electrode 28 and displaces the blood from the area around each electrode 28 in which the electric field is located.

Figure 15:
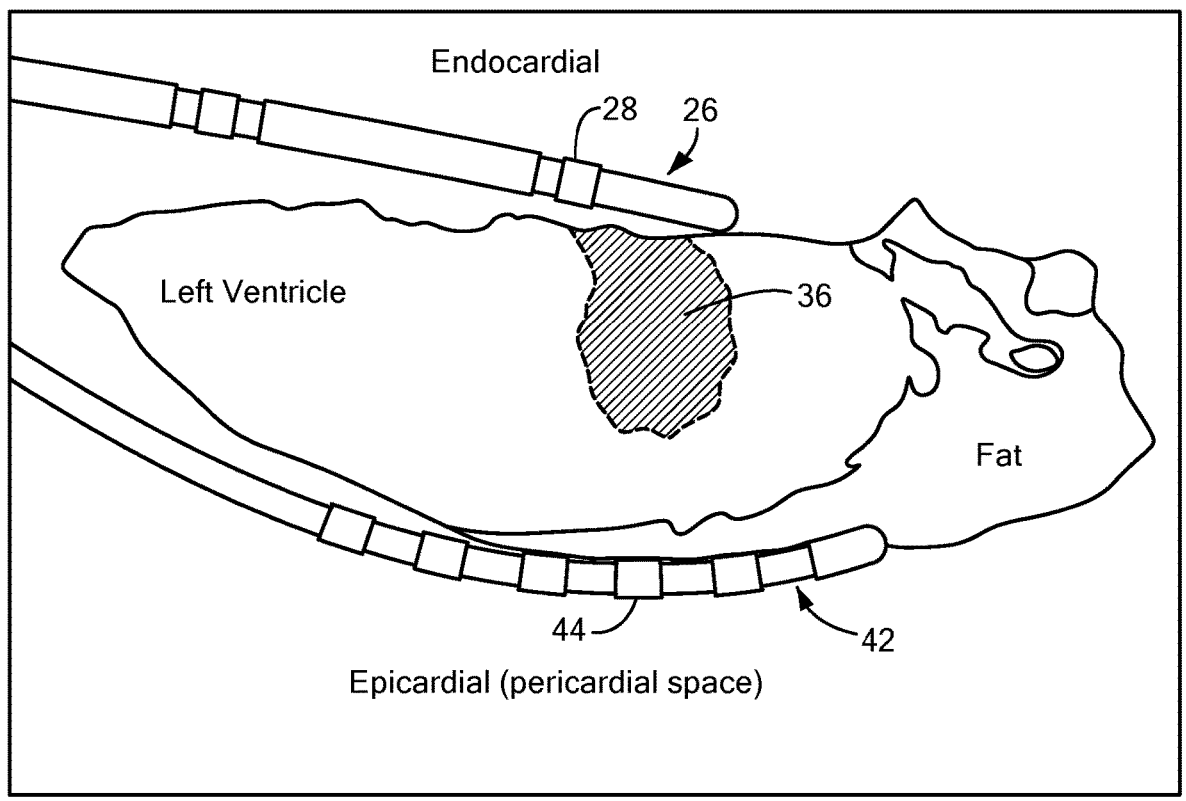
FIG. 15 shows an exemplary placement of an energy delivery device and a secondary device relative to myocardial tissue.
Figure 16:
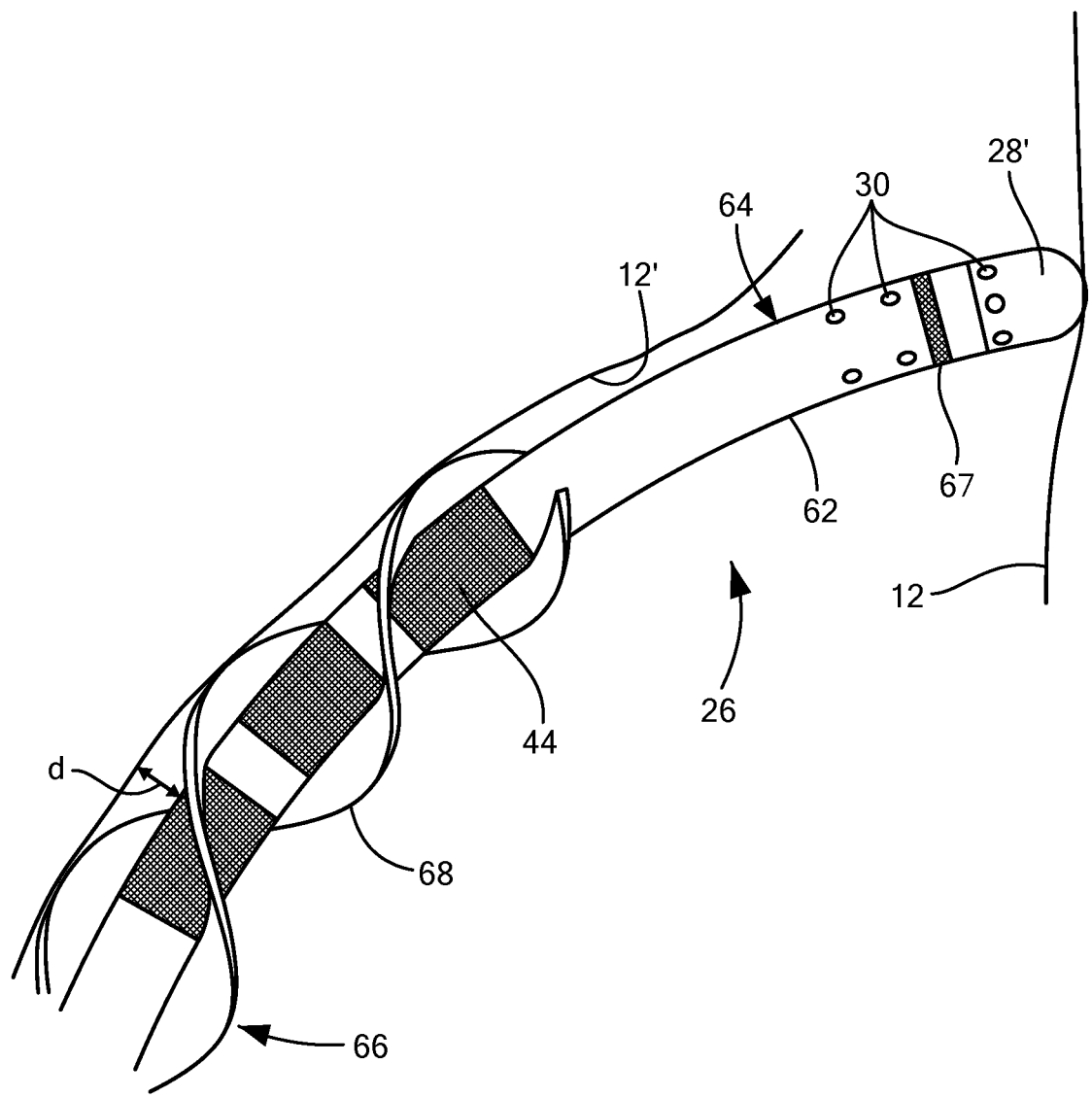
FIG. 16 shows a first embodiment of an energy delivery device, the device including at least one energy return electrode and at least one distancing element.
Figure 17:
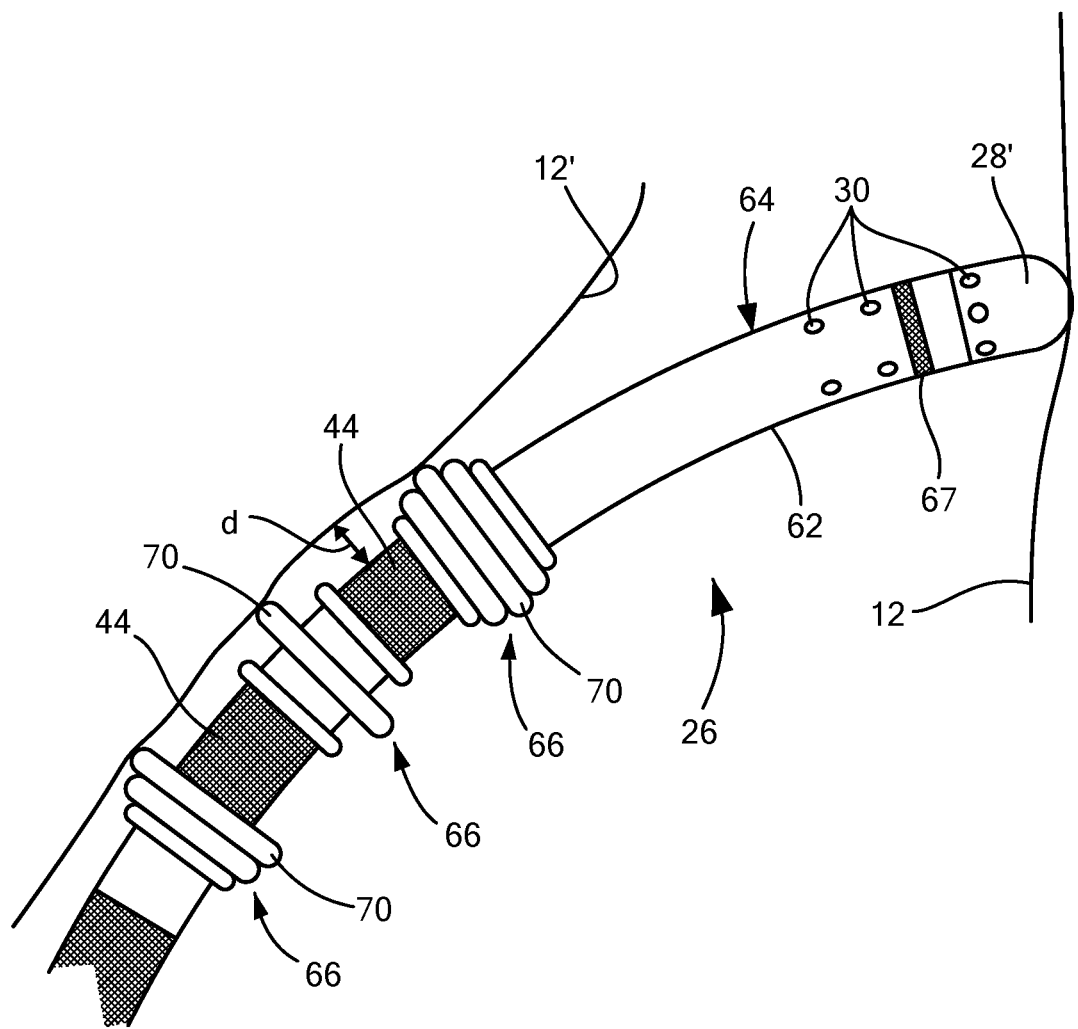
FIG. 17 shows a second embodiment of an energy delivery device, the device including at least one energy return electrode and at least one distancing element.
Figure 18:
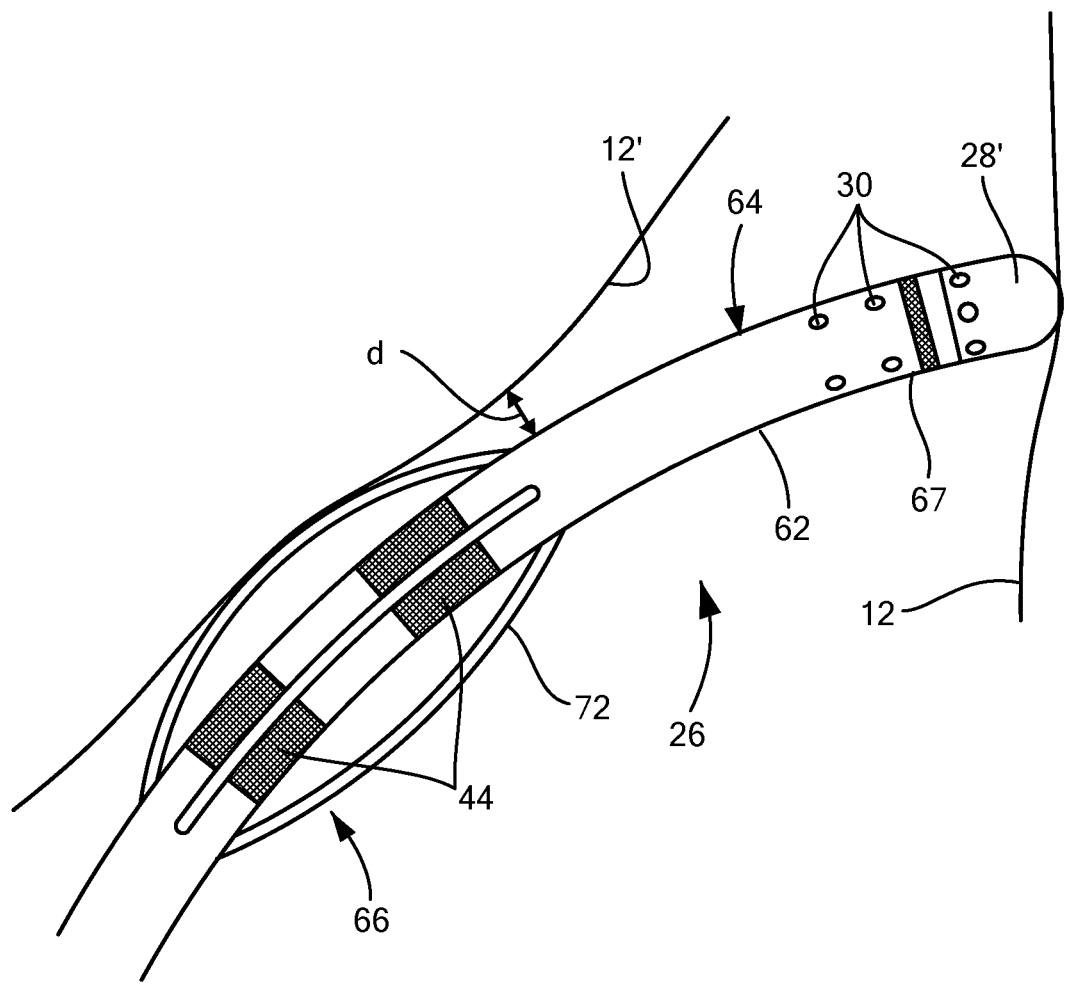
FIG. 18 shows a third embodiment of an energy delivery device, the device including at least one energy return electrode and at least one distancing element.

Referring now to FIGS. 13-15, the focal delivery of bipolar pulsed field ablation energy is shown, with FIG. 14 also showing the delivery of impedance-modifying fluid 24. In both FIGS. 13 and 14, energy is delivered from a focal medical device, such as an energy delivery device 26 configured to deliver pulsed field ablation energy 10. In one embodiment, the energy delivery device 26 has an elongate body 62 with a distal portion 64, a proximal portion opposite the distal portion, and an energy delivery electrode 28 at the distal portion 64 (for example, at the distal end of the elongate body 62). An energy return electrode 44 is also used, which has a larger surface area than the energy delivery electrode 28 of the energy delivery device 26. The energy delivery electrode 28 provides a first (for example, positive) polarity, whereas the energy return electrode 44 provides a second (for example, negative) polarity, such that the pulsed field ablation energy 10 delivered to the target tissue 12 from the energy delivery electrode 28 flows to the energy return electrode 44. The energy return electrode 44 may be one or more energy return electrodes 44 on a secondary device 42 (for example, as shown in FIGS. 13 and 14) and/or on the energy delivery device 26 (for example, as shown in FIGS. 16-18). In one embodiment, the energy return electrode 44 is on a sheath. In another embodiment, the energy return electrode is on an in-dwelling device, which may reduce skeletal muscle stimulation, depending on pulse parameters, and subsequent need for paralytic agents and/or injury risk to the patient and/or the user from unintended muscle stimulations. In another embodiment, the energy return electrode is a ground patch applied to the patient's skin. However, any combination of energy return electrodes 44 may also be used.

In another embodiment, as shown in FIG. 15, the secondary device 42 may be positioned within the pericardial space to serve as a ground plane for delivery of pulsed field ablation energy from the energy delivery device 26, positioned within a heart chamber. As such, the energy return electrode 44 may be segmented, or the secondary device 42 may include a plurality of energy return electrodes 44, such that the user may select/activate multiple segments of the energy return electrode 44, or multiple energy return electrodes 44, for a relatively larger surface area compared to the energy delivery electrode 28, or the user may select/activate fewer segments of the energy return electrode 44, or fewer energy return electrodes 44, for a smaller surface area to serve as an opposing electrode in an endocardial-to-epicardial ablation vectoring arrangement. When the active surface areas of the energy delivery electrode(s) 28 and the energy return electrode(s) 44 are similar or the same, the lesion 36 formed in the tissue may form from both sides, endocardial and epicardial, meeting the mid-myocardium in a continuous transmural lesion. When a relatively larger active surface area of the energy return electrode 44 is selected/activated, the lesion 36 will extend from the endocardium to some depth within the mid-myocardium, but minimal lesion formation may occur from the epicardial aspect (for example, as shown in FIG. 15). Additionally, it may be advantageous to inject a hypertonic solution (such as a hypertonic saline solution) into the pericardial space adjacent to the energy return electrode(s) 44 to create a larger active surface area with reduced overall impedance.

As is shown in FIGS. 13 and 14, the delivery of an impedance-modifying fluid 24 immediately before and/or during the delivery of pulsed field ablation energy 10 enhances lesion size and depth, even during the focal delivery of bipolar ablation energy using an energy return electrode. In one embodiment, the energy delivery device 26 includes one or more irrigation ports 30 proximal to the energy delivery electrode 28. As shown in FIG. 14, the delivery of a hypotonic impedance-modifying fluid 24 from the irrigation port(s) 30 will direct the electrical current 10 away from the area of increased impedance, toward and through the target tissue 12. Thus, the delivery of an impedance-modifying fluid 24 immediately before and/or during the delivery of pulsed field ablation energy 10 creates deeper lesions 36 (for example, as shown in FIG. 14) than the lesions 34 created without the use of impedance-modifying fluid 24 (for example, as shown in FIG. 13).

Referring now to FIGS. 16-18, embodiments of an energy delivery device 26 are shown, the energy delivery device 26 including at least one energy return electrode 44 and at least one distancing element 66. As noted above, the at least one energy return electrode 44 may include one or more energy return electrodes 44 on the energy delivery device 26. In the embodiments shown in FIG. 16-18, the energy delivery device 26 includes an elongate body 62 having an energy delivery electrode 28 at a distal portion 64 and a plurality of energy return electrodes 44 along the elongate body 62 proximal to the energy delivery electrode 28. As shown in FIG. 16, the energy delivery electrode 28 may be a distal tip electrode 28', but it will be understood that the energy delivery electrode 28 may additionally or alternatively be an electrode located proximal to the distal tip of the elongate body 62). The energy delivery device 26 optionally also includes one or more irrigation ports 30 for the delivery of impedance-modifying fluid 24. Pulsed field ablation energy 10 delivered from the energy delivery electrode 28 to the target tissue 12 may flow toward the plurality of energy return electrodes 44 as shown in FIGS. 13 and 14. Further, each energy return electrode 44 may be in electrical communication with and individually controllable by the control unit 40 (during automatic or semi-automatic system operation) and/or the user (during manual system operation). In one embodiment, the energy delivery electrode 28 and/or additional electrode(s) 67 (such as mapping electrodes) at the distal portion 64 of the elongate body 62 are used to record electrograms (EGMs) from the target tissue 12 and transmit the data to the control unit 40. Additionally or alternatively, the control unit 40 and/or the user selectively activates or deactivates individual energy return electrodes 44 based on their location with respect to the energy delivery electrode(s) 28, in order to achieve a desired energy delivery vector pathway, potentially avoiding non-targeted structures such as nerves or skeletal muscles, and also to create a desired ablation pattern or lesion depth. For example, the control unit 40 may compare the recorded EGMs to a threshold EGM value and selectively activate or deactivate individual energy return electrodes 44 based on the comparison. The control unit 40 may also be configured to alert the user and/or prevent the delivery of pulsed field ablation energy if the control unit 40 determines that too few energy return electrodes 44 are activated. The control unit 40 may also collect positional navigation information via electromagnetic or electric potential navigation systems that would define the relative physical locations in space of the energy delivery 28 and energy return 44 electrode(s).

In the embodiments shown in FIGS. 16-18, the energy delivery device 26 also includes at least one distancing element 66. Each distancing element 66 is composed of non-conductive material, such as plastic, silicone, rubber, or the like. Further, each distancing element 66 maintains a distance d between the energy return electrode(s) 44 and non-target tissue 12' with which the energy return electrode(s) 44 may come into contact during the energy delivery procedure. Put another way, each distancing element 66 has an outer diameter that is greater than the outer diameter of the energy return electrode 44. Referring to FIG. 16, at least one distancing element 66 includes a plurality of fins 68 that are spiraled around at least a portion of the elongate body 62. However, the distancing elements 66 may have other configurations, including, but not limited to, those shown in FIGS. 17 and 18.

Referring to FIG. 17, each distancing element 66 includes one or more rings 70. In one embodiment, each distancing element 66 includes a plurality of rings 70 having a variety of outer diameters, such that each distancing element 66 is tapered in at least one of a proximal-to-distal direction and a distal-to-proximal direction. Additionally or alternatively, each distancing element 66 includes a single ring 70 having a diameter that is greater than an outer diameter of the elongate body 62 proximate the distancing element 66. Additionally or alternatively, referring to FIG. 18, each distancing element 66 includes one or more curved or bowed splines 72 extending in a direction parallel to the elongate body 62. However, it will be understood that other configurations may be used, provided each distancing element 66 is sized and configured to maintain a distance d between the energy return electrode(s) 44 and the non-targeted tissue 12'. Further, each distancing element 66 may be transitionable between a delivery configuration and an expanded configuration. In the delivery configuration, the distancing element 66 is positioned immediately proximate or against the elongate body 62 to facilitate navigation through the patient's vasculature and to reduce the likelihood of patient injury. Exemplary expanded configurations are shown in FIGS. 16-18. The distancing elements 66 may be in mechanical communication with one or more actuation elements (for example, one or more rods, pull wires, knobs, or the like) that enable the user to transition the distancing elements 66 between the delivery configuration and the expanded configuration. Additionally or alternatively, the distancing elements 66 may be composed of a flexible or highly flexible material that is biased toward the expanded configuration, but that allows the distancing elements 66 to be easily compressed against the elongate body 62 during navigation to the treatment site (delivery configuration) without damage to surrounding tissue.

In a first step of an exemplary method of delivering pulsed field ablation energy and an impedance-modifying fluid 24, at least one energy delivery electrode 28 of an energy delivery device 26 is positioned within the patient's body proximate an area of target tissue 12. In an optional second step, at least one energy return electrode 44 is positioned at a desired distance from the at least one energy delivery electrode 28. In one embodiment, the at least one energy return electrode 44 is on or coupled to the energy delivery device 26 (for example, as shown in FIGS. 16-18). Additionally or alternatively, the at least one energy return electrode 44 is located on a secondary device 42, such as an in-dwelling device, and/or affixed to an external surface of the patient's body. In an optional third step, EGMs are recorded from the target tissue 12 by the energy delivery electrode 28 and/or one or more mapping electrodes on, coupled to, or otherwise borne on the energy delivery device 26 and/or a secondary mapping device. The EGM data is then transmitted from the energy delivery device 26 and/or secondary mapping device 42 to the control unit 40, where the processing circuitry 48 may use the EGM data to determine whether to selectively activate or deactivate one or more of the at least one energy return electrodes 44 and/or display an alert or suggestion to the user for the manual activation or deactivation of one or more of the at least one energy return electrode 44 (for example, through a user input device 50 in communication with or included in the control unit 40). Additionally, EGMs may continue to be recorded and the activation/deactivation of the at least one energy return electrode 44 modified during and/or after the delivery of pulsed field ablation energy 10.

In a first exemplary fourth step, the processing circuitry 48 instructs the pump 54 to deliver a bolus or volume of at least one impedance-modifying fluid 24 from the energy delivery device 26 at a location proximate the target tissue/treatment site 12. In one embodiment, the processing circuitry 48 instructs the pump 54 to deliver a volume of hypotonic fluid of approximately 4 mL over a period of approximately two seconds. In another embodiment, the processing circuitry instructs the pump 54 to deliver a first volume of hypotonic fluid 24 and a second volume of hypertonic fluid 24' (for example, as shown in FIG. 11). Optionally, the impedance-modifying fluid 24 may be evacuated from the treatment site 12 during or after the delivery of the impedance-modifying fluid 24 and after the delivery of pulsed field ablation energy. The energy return electrode(s) 44 provide a low-impedance, large conductive area that, in general, does not achieve a high enough electric field strength around them to ablate adjacent tissue. Delivery of the second impedance-modifying fluid 24' with a higher electrical conductivity to regions around the energy return electrode(s) 44 increases the effective conductivity of the energy return path and reduces the potential for local field gradients to achieve ablation threshold field gradients, especially at points where the metal energy return electrode(s) 44 are in contact with non-targeted tissue. Delivery of a hypertonic solution (such as the second impedance-modifying fluid 24') around the return path electrodes (for example, 2% saline solution) in such situations may be advantageous.

In a first exemplary fifth step, the processing circuitry 48 instructs the energy generator 46 to deliver pulsed field ablation energy (electric current) 10 from the at least one energy delivery electrode 28 to the target tissue 12 after a duration of approximately two seconds from the delivery of the impedance-modifying fluid 24 has occurred. That is, the impedance-modifying fluid 24 is delivered to the treatment site 12 immediately before, or approximately two seconds before, the delivery of at least a first pulse of electric current 10 (that is, first pulse of pulsed field ablation energy 10). In one embodiment, between approximately 1 mL (±0.2 mL) and approximately 6 mL (±0.2 mL) is delivered to the treatment site at a delivery rate of approximately 1 mL/sec to approximately 2 mL/sec.

In a second exemplary fourth step, and in addition to or instead of the first exemplary fourth step, the processing circuitry 48 instructs the pump 54 and the energy generator 46 to deliver the impedance-modifying fluid 24 and the pulsed field ablation energy 10, respectively, simultaneously, such that the impedance-modifying fluid 24 and the electric current 10 are delivered to the treatment site 12 at the same time. The impedance-modifying fluid 24 is delivered as a small volume and/or for a short duration. For example, the impedance-modifying fluid 24 is delivered at a rate of approximately 1 mL/min to approximately 2 mL/sec. Optionally, one or more additional volumes of impedance-modifying fluid 24 are delivered to the treatment site 12 during the delivery of the pulsed field ablation energy. Optionally, the impedance-modifying fluid 24 may be evacuated from the treatment site 12 during or after the delivery of pulsed field ablation energy.

Although these steps include the delivery of an impedance-modifying fluid 24, it will be understood that pulsed field ablation energy 10 may be delivered to the treatment site before the delivery of the impedance-modifying fluid 24, or after the volume of impedance-modifying fluid 24 has dissipated from the treatment site 12. This may allow the user greater control over the creation of lesions of various depths and sizes and/or to modification of the size or depth of a previously created lesion. Additionally, one or both of a hypotonic and hypertonic fluid may be used. If a mixture of hypotonic and hypertonic fluids is used, the relative concentrations of each fluid may be adjusted before and/or during the delivery of pulsed field ablation energy to create the desired lesion size and/or depth.

In a sixth step, the energy delivery device 26, and any secondary devices, are removed from within the patient's body.

In one embodiment, a system for ablating tissue at a treatment site comprises: an energy delivery device; and a control unit including: a source of impedance-modifying fluid in fluid communication with the energy delivery device; an energy generator in electrical communication with the energy delivery device, the energy generator being configured to transmit energy to the energy delivery device and the energy delivery device being configured to deliver energy to the treatment site; and processing circuitry configured to control delivery of the impedance-modifying fluid from the energy delivery device to the treatment site.

In one aspect of the embodiment, the processing circuitry is configured to control delivery of the impedance-modifying fluid from the energy delivery device such that the energy delivery device delivers the impedance-modifying fluid to the treatment site before an onset of the delivery of energy from the energy delivery device to the tissue site. In one aspect of the embodiment, the energy delivery device delivers the impedance-modifying fluid to the treatment site at a flow rate of between approximately 1 mL/min to approximately 120 mL/min (approximately 2 mL/sec). In one aspect of the embodiment, the energy delivery device delivers the impedance-modifying fluid to the treatment site approximately two seconds before the onset of the delivery of energy from the energy delivery device to the tissue site.

In one aspect of the embodiment, the processing circuitry is configured to control delivery of the impedance-modifying fluid from the energy delivery device such that the energy delivery device delivers the impedance-modifying fluid to the treatment site simultaneously with an onset of the delivery of energy from the energy delivery device to the tissue site.

In one aspect of the embodiment, the impedance-modifying fluid is a hypotonic fluid. In one aspect of the embodiment, the hypotonic fluid is an aqueous solution of saline including less than 0.9% by weight of sodium chloride.

In one embodiment, the hypotonic fluid includes at least one of glucose, dextrose, calcium, calcium gluconate, and calcium chloride.

In one aspect of the embodiment, the impedance-modifying fluid is a hypertonic fluid.

In one aspect of the embodiment, the energy delivery device includes at least one irrigation port in fluid communication with the source of impedance-modifying fluid. In one aspect of the embodiment, the energy delivery device further includes at least one energy delivery electrode, the at least one irrigation port being at least one of in the at least one electrode and in close proximity to the at least one electrode.

In one aspect of the embodiment, each of the at least one energy delivery electrode has a first edge and a second edge proximal to the first end, the at least one irrigation port being in the electrode immediately proximate at least one of the first edge and the second edge.

In one aspect of the embodiment, the energy delivery device further includes an electrode-bearing structure to which the at least one electrode is coupled, the at least one irrigation port being in the electrode-bearing structure.

In one aspect of the embodiment, the source of impedance-modifying fluid is a source of a first impedance-modifying fluid, the control unit further including a source of a second impedance-modifying fluid in fluid communication with the energy delivery device. In one aspect of the embodiment, the first impedance-modifying fluid is a hypotonic fluid and the second impedance-modifying fluid is a hypertonic fluid, the processing circuitry being configured to control delivery of the first and second impedance-modifying fluids from the energy delivery device such that the energy delivery device delivers the first impedance-modifying fluid to a first portion of the treatment site and delivers the second impedance-modifying fluid to a second portion of the treatment site simultaneously.

In one aspect of the embodiment, the first impedance-modifying fluid is a hypotonic fluid and the second impedance-modifying fluid is a hypertonic fluid, the energy delivery device being configured to deliver first and second impedance-modifying fluids together as a mixture, the processing circuitry being configured to modify the amount of at least one of the first impedance-modifying fluid and the second impedance-modifying fluid to change the mixture during at least one of before and during the delivery of energy from the energy delivery device.

In one embodiment, a method for ablating tissue comprises delivering an impedance-modifying fluid to a treatment site and delivering pulsed field ablation energy to the treatment site.

In one aspect of the embodiment, the treatment site includes an area of target tissue and blood in contact with the area of target tissue, the pulsed field ablation energy being delivered to the area of target tissue and the impedance-modifying fluid being delivered to the blood.

In one aspect of the embodiment, the impedance-modifying fluid is delivered to the blood immediately before the pulsed field ablation energy is delivered to the area of target tissue.

In one aspect of the embodiment, the impedance-modifying fluid is delivered to the blood simultaneously with the delivery of pulsed field ablation energy to the area of target tissue.

In one aspect of the embodiment, the treatment site includes an area of epicardial tissue and a pericardial space in contact with the area of epicardial tissue, the pulsed filed ablation energy being delivered to the area of epicardial tissue and the impedance-modifying fluid being delivered to the pericardial space.

In one embodiment, a tissue ablation device comprises: an elongate body having a distal portion and a proximal portion opposite the distal portion, the distal portion including a distal end; an energy delivery electrode at the distal portion of the elongate body; an energy return electrode on the elongate body proximal to the energy delivery electrode; and a distancing element on the elongate body proximate the energy return electrode.

In one aspect of the embodiment, the distancing element has a first outer diameter and the energy return electrode has a second outer diameter that is less than the first outer diameter.

In one aspect of the embodiment, the distancing element is composed of a non-conductive material. In one aspect of the embodiment, the distancing element is at least one of a fin, a ring, and a spline.

In one aspect of the embodiment, the distancing element is transitionable between a delivery configuration and an expanded configuration.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for ablating tissue at a treatment site, the system comprising:
   an energy delivery device comprising:
      a distal tip, the distal tip defining a first plurality of irrigation ports;
      an energy delivery electrode, the energy delivery electrode being proximal to the distal tip and defining a second plurality of irrigation ports;
      a first chamber in fluid communication with the first plurality of irrigation ports, the first chamber being proximate the energy delivery electrode;
      a second chamber having a same diameter as a diameter of the first chamber, the second chamber being in fluid communication with the second plurality of irrigation ports, the first chamber being disposed proximate the second chamber;
   a control unit including:
      a first source of first impedance-modifying fluid in fluid communication with only the first plurality of irrigation ports;
      a second source of second impedance-modifying fluid in fluid communication with only the second plurality of irrigation ports, wherein the first impedance-modifying fluid is a hypertonic fluid and the second impedance-modifying fluid is a hypotonic fluid;
      an energy generator in electrical communication with the energy delivery electrode, the energy generator being configured to transmit energy to the energy delivery electrode and the energy delivery electrode being configured to deliver energy to the treatment site; and
      processing circuitry configured to control delivery of the impedance-modifying fluid from the first source and the second source to the energy delivery device.

2. The system of claim 1, wherein the processing circuitry is configured to control delivery of the first impedance-modifying fluid and the second impedance-modifying fluid from the first source and the second source respectively to the energy delivery device such that the energy delivery device delivers the first impedance-modifying fluid and the second impedance-modifying fluid to the treatment site before an onset of a delivery of energy from the energy delivery device to the treatment site.

3. The system of claim 2, wherein the energy delivery device is configured to deliver the first impedance-modifying fluid and the second impedance-modifying fluid to the treatment site at a flow rate of between approximately 1 mL/min to approximately 2 mL/sec.

4. The system of claim 3, wherein the energy delivery device is configured to deliver the first impedance-modifying fluid and the second impedance-modifying fluid to the treatment site for approximately two seconds before the onset of the delivery of energy from the energy delivery device to the treatment site.

5. The system of claim 1, wherein the processing circuitry is configured to control delivery of the first impedance-modifying fluid and the second impedance-modifying fluid from the energy delivery device such that the energy delivery device delivers the first impedance-modifying fluid and the second impedance-modifying fluid to the treatment site simultaneously with an onset of the delivery of energy from the energy delivery device to the treatment site.

6. The system of claim 1, wherein the hypotonic fluid is an aqueous solution of saline and includes less than 0.9% by weight of sodium chloride.

7. The system of claim 1, wherein the hypotonic fluid includes at least one of glucose, dextrose, calcium, calcium gluconate, and calcium chloride.

8. The system of claim 1, further comprising an electrode-bearing structure disposed proximate the energy delivery electrode, the electrode-bearing structure defining a third plurality of irrigation ports.

9. The system of claim 1, wherein each individual irrigation port from the first plurality of irrigation ports is the same size as each individual irrigation port from the second plurality of irrigation ports.

10. The system of claim 1, wherein the processing circuitry is configured to control delivery of the first and second impedance-modifying fluids from the first source and the second source such that the energy delivery device delivers the first impedance-modifying fluid to the first plurality of irrigation ports and delivers the second impedance-modifying fluid to the second plurality of irrigation ports simultaneously.

11. The system of claim 1, wherein the energy delivery device is configured to deliver the first and second impedance-modifying fluids together as a mixture, the processing circuitry being configured to modify an amount of at least one of the first impedance-modifying fluid and the second impedance-modifying fluid to change the mixture during at least one of before and during a delivery of energy from the energy delivery device.

12. A method for ablating tissue comprising:
delivering a first volume of a first impedance-modifying fluid to a treatment site from a first source of the first impedance-modifying fluid in fluid communication with a first plurality of irrigation ports;
delivering a second volume of a second impedance-modifying fluid to the treatment site from a second source of the second impedance-modifying fluid in fluid communication with only the second plurality of irrigation ports, wherein the first impedance-modifying fluid is a hypertonic fluid and the second impedance-modifying fluid is a hypotonic fluid;
the first volume of the first impedance-modifying fluid being delivered through to only the first plurality of irrigation ports disposed on a distal tip of an electrode bearing surface, the first chamber being disposed proximate a plurality of energy delivery electrodes;
the second volume of the second impedance-modifying fluid being delivered through a second chamber having a same diameter as a diameter of the first chamber to only the second plurality of irrigation ports defined by the plurality of energy delivery electrodes coupled to the electrode bearing surface and disposed on the plurality of energy delivery electrodes coupled to the electrode bearing surface, the first chamber being disposed proximate the second chamber; and
delivering pulsed field ablation energy to the treatment site.

13. The method of claim 12, wherein the treatment site includes an area of target tissue and blood in contact with the area of target tissue, the pulsed field ablation energy being delivered to the area of target tissue and the first and second impedance-modifying fluid being delivered to the blood.

14. The method of claim 13, wherein the first impedance-modifying fluid is delivered to the blood immediately before the pulsed field ablation energy is delivered to the area of target tissue.

15. The method of claim 13, wherein the second impedance-modifying fluid is delivered to the blood simultaneously with the delivery of pulsed field ablation energy to the area of target tissue.

16. The method of claim 12, wherein the treatment site includes an area of epicardial tissue and a pericardial space in contact with the area of epicardial tissue, the pulsed field ablation energy being delivered to the area of epicardial tissue and the first and the second impedance-modifying fluid being delivered to the pericardial space.

17. A tissue ablation device comprising:
an elongate body having a fluid delivery conduit, a first chamber, a second chamber, a distal portion, and a proximal portion opposite the distal portion, the distal portion including a distal end, the distal end having a distal tip, the distal tip defining a first plurality of irrigation ports configured to provide a first volume of a first impedance-modifying fluid from a first source of the first impedance-modifying fluid in fluid communication with the first plurality of irrigation ports;
an energy delivery electrode at the distal portion of the elongate body and being disposed proximate the second chamber, the energy delivery electrode defining a second plurality of irrigation ports configured to provide a second volume of a second impedance-modifying fluid from a second source of the second impedance-modifying fluid in fluid communication with the second plurality of irrigation ports, wherein the first impedance-modifying fluid is a hypertonic fluid and the second impedance-modifying fluid is a hypotonic fluid,
the first chamber being in fluid communication with the first plurality of irrigation ports,
the second chamber having a same diameter as a diameter of the first chamber, the second chamber being in fluid communication with the second plurality of irrigation ports,
the first chamber being disposed proximate the second chamber and the first chamber being proximate the energy delivery electrode;
an energy return electrode on the elongate body proximal to the energy delivery electrode, the energy return electrode having a first outer diameter; and
a distancing element on the elongate body proximate the energy return electrode, the distancing element having a plurality of curved splines, each curved spline extending in a direction parallel to the elongate body and having a second outer diameter that is greater than the first outer diameter.

18. The tissue ablation device of claim 17, wherein the distancing element is transitionable between a delivery configuration and an expanded configuration, the distancing element having the second outer diameter when the distancing element is in the expanded configuration.

* * * * *